(12) United States Patent
Gagner et al.

(10) Patent No.: US 9,421,015 B2
(45) Date of Patent: Aug. 23, 2016

(54) INCISIONLESS GASTRIC BYPASS METHOD AND DEVICES

(75) Inventors: Michel Gagner, Montréal (CA); David J. Blaeser, Brooklyn Park, MN (US); Todd A. Krinke, Buffalo, MN (US); Philip J. Haarstad, Chanhassen, MN (US)

(73) Assignee: Michel Gagner, Montréal, Q.C. (CA)

( * ) Notice: Subject to any disclaimer, the term of this patent is extended or adjusted under 35 U.S.C. 154(b) by 907 days.

(21) Appl. No.: 13/528,649

(22) Filed: Jun. 20, 2012

(65) Prior Publication Data

US 2012/0330330 A1 Dec. 27, 2012

Related U.S. Application Data

(62) Division of application No. 12/837,392, filed on Jul. 15, 2010, now abandoned.

(60) Provisional application No. 61/226,225, filed on Jul. 16, 2009, provisional application No. 61/225,901, filed on Jul. 15, 2009.

(51) Int. Cl.
| | |
|---|---|
| *A61B 17/94* | (2006.01) |
| *A61B 17/11* | (2006.01) |
| *A61B 17/221* | (2006.01) |
| *A61B 17/00* | (2006.01) |
| *A61B 17/29* | (2006.01) |

(52) U.S. Cl.
CPC .......... *A61B 17/1114* (2013.01); *A61B 17/221* (2013.01); *A61B 2017/0034* (2013.01); *A61B 2017/00278* (2013.01); *A61B 2017/00296* (2013.01); *A61B 2017/00336* (2013.01); *A61B 2017/00358* (2013.01); *A61B 2017/00477* (2013.01); *A61B 2017/00876* (2013.01); *A61B 2017/1117* (2013.01); *A61B 2017/1139* (2013.01); *A61B 2017/2926* (2013.01)

(58) Field of Classification Search
CPC ............................................... A61B 2017/1117
See application file for complete search history.

(56) References Cited

U.S. PATENT DOCUMENTS

| | | | |
|---|---|---|---|
| 3,358,676 A | * | 12/1967 | Frei et al. ........................ 600/12 |
| 5,595,562 A | | 1/1997 | Grier |
| 5,690,656 A | | 11/1997 | Cope et al. |

(Continued)

FOREIGN PATENT DOCUMENTS

WO   WO 2009/082710 A1   7/2009

OTHER PUBLICATIONS

United States Patent and Trademark Office, Office Action mailed May 10, 2012 in U.S. Appl. No. 12/837,392, 28 pages.

(Continued)

*Primary Examiner* — Paula L. Craig
(74) *Attorney, Agent, or Firm* — Inskeep IP Group, Inc.

(57) ABSTRACT

A system and method for endoscopically forming an anastomosis between two naturally adjacent points in the digestive tract. The system and method utilizes elongate magnetic devices that, when connected across a tissue boundary, necrose tissue until an anastomosis forms and the devices are passed naturally. Despite the elongate shape of the devices, the resulting anastomosis is substantially round. As such, round anastomoses can be formed having increased diameters merely by increasing the lengths of the devices, obviating the need for wider endoscopes.

5 Claims, 27 Drawing Sheets

(56) References Cited

U.S. PATENT DOCUMENTS

| | | | |
|---|---|---|---|
| 6,352,543 B1* | 3/2002 | Cole | 606/153 |
| 6,632,229 B1* | 10/2003 | Yamanouchi | 606/153 |
| 7,211,094 B2 | 5/2007 | Gannoe et al. | |
| 7,282,057 B2 | 10/2007 | Surti et al. | |
| 7,654,951 B2* | 2/2010 | Ishikawa | 600/114 |
| 7,938,841 B2* | 5/2011 | Sharkawy et al. | 606/153 |
| 2002/0072758 A1* | 6/2002 | Reo et al. | 606/153 |
| 2003/0225312 A1* | 12/2003 | Suzuki et al. | 600/114 |
| 2004/0225191 A1* | 11/2004 | Sekine et al. | 600/178 |
| 2007/0135802 A1* | 6/2007 | Suzuki | 606/1 |
| 2007/0260214 A1 | 11/2007 | Mikkaichi et al. | |
| 2008/0114384 A1 | 5/2008 | Chang et al. | |
| 2008/0208224 A1 | 8/2008 | Surti et al. | |
| 2009/0125042 A1 | 5/2009 | Mouw | |
| 2009/0227828 A1* | 9/2009 | Swain et al. | 600/12 |
| 2010/0036399 A1* | 2/2010 | Viola | 606/153 |
| 2010/0179510 A1* | 7/2010 | Fox | A61B 17/11 604/509 |
| 2010/0256659 A1* | 10/2010 | Aguirre et al. | 606/153 |
| 2011/0009886 A1* | 1/2011 | Gagner et al. | 606/153 |
| 2011/0144560 A1* | 6/2011 | Gagner et al. | 604/8 |
| 2012/0259350 A1* | 10/2012 | Gagner et al. | 606/153 |
| 2013/0138126 A1* | 5/2013 | Gagner et al. | 606/153 |
| 2013/0150873 A1* | 6/2013 | Gagner et al. | 606/153 |

OTHER PUBLICATIONS

WIPO, U.S. International Search Authority, International Search Report and Written Opinion mailed Sep. 14, 2010 in International Patent Application No. PCT/US2010/042180, 12 pages.

* cited by examiner

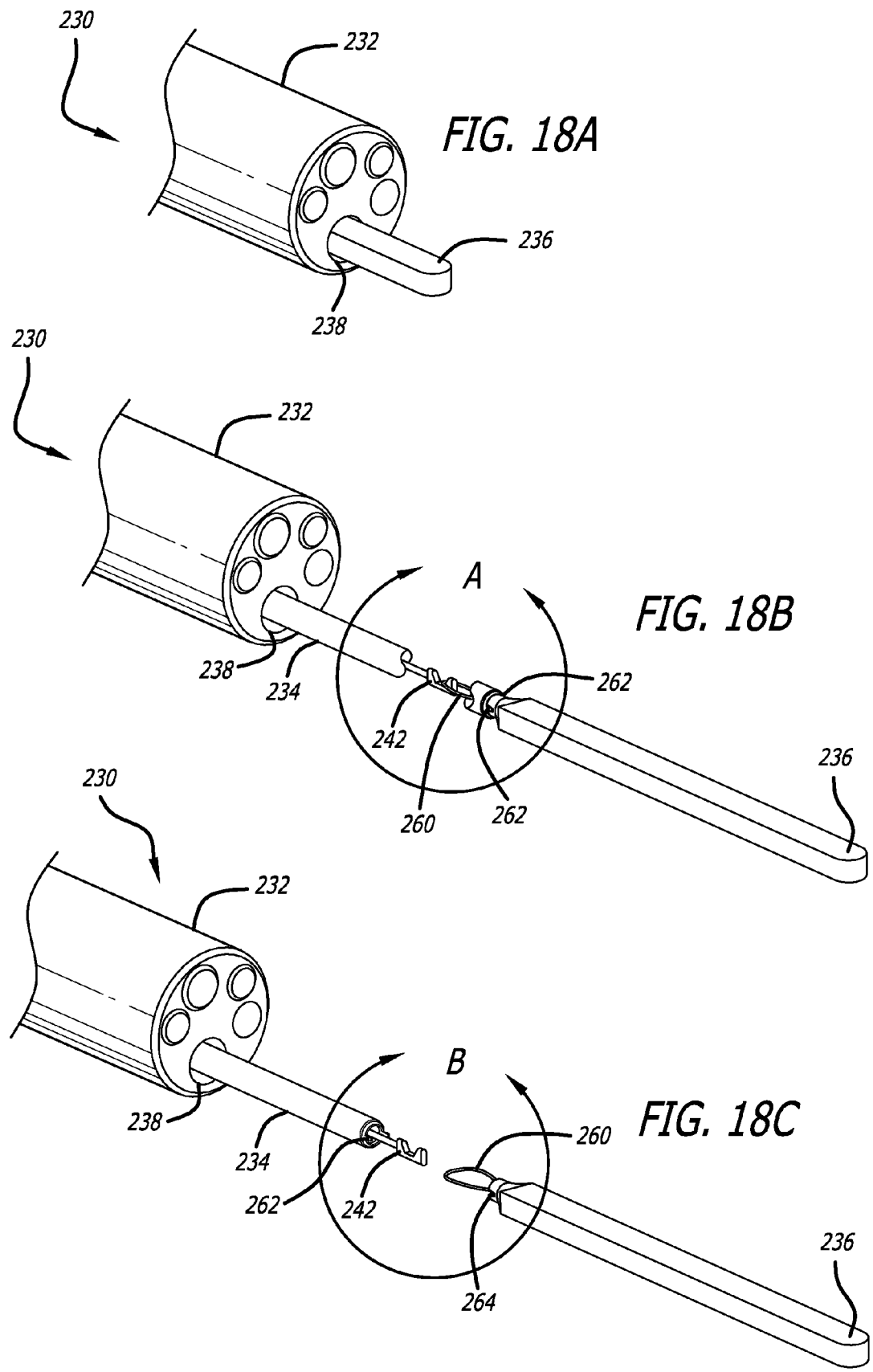

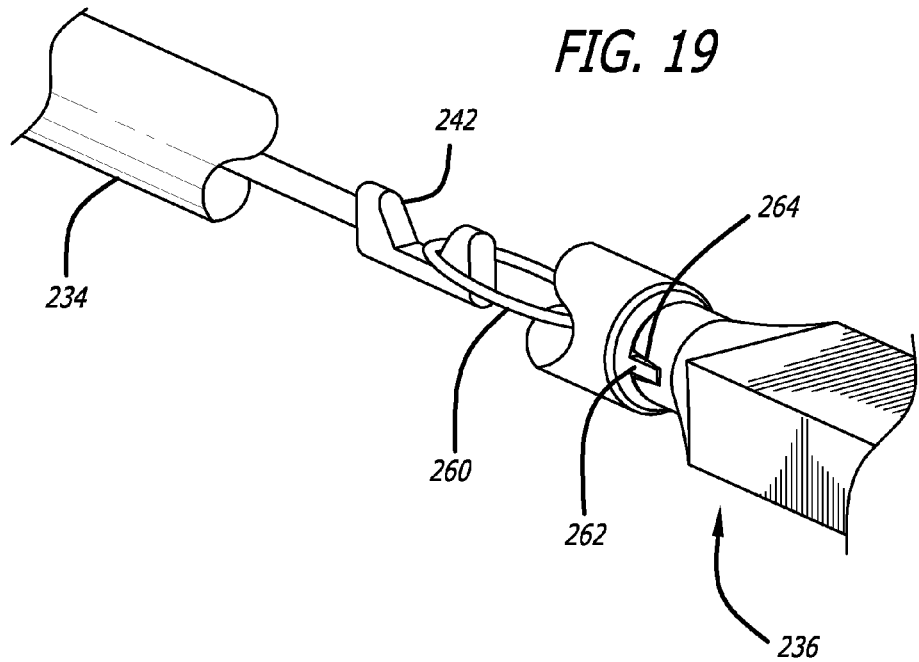
FIG. 19
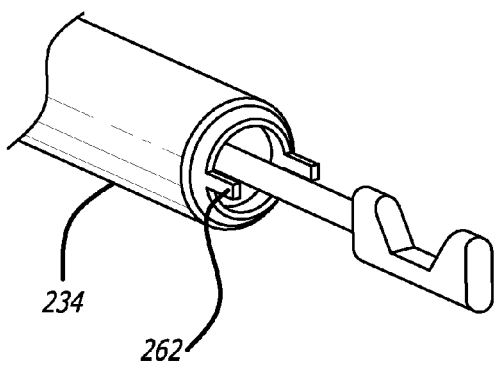
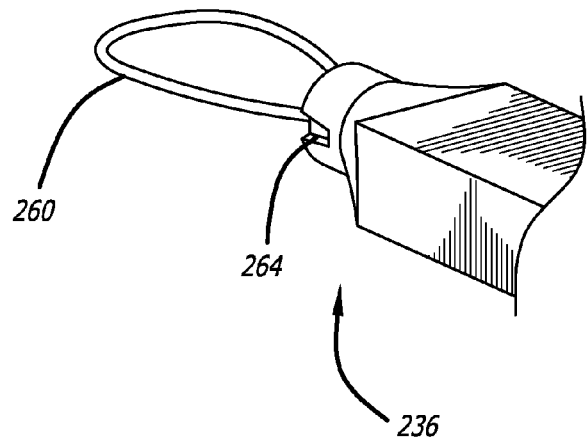
FIG. 20

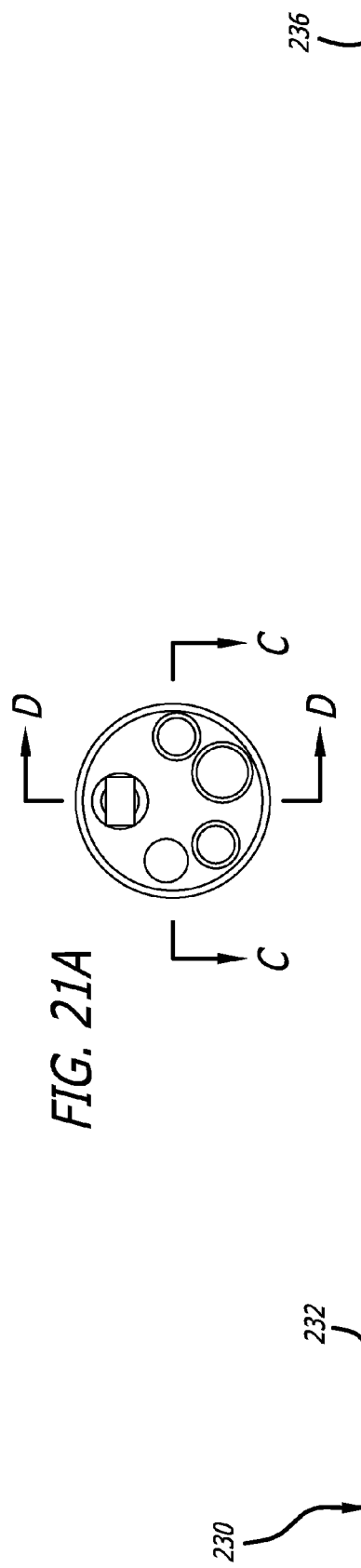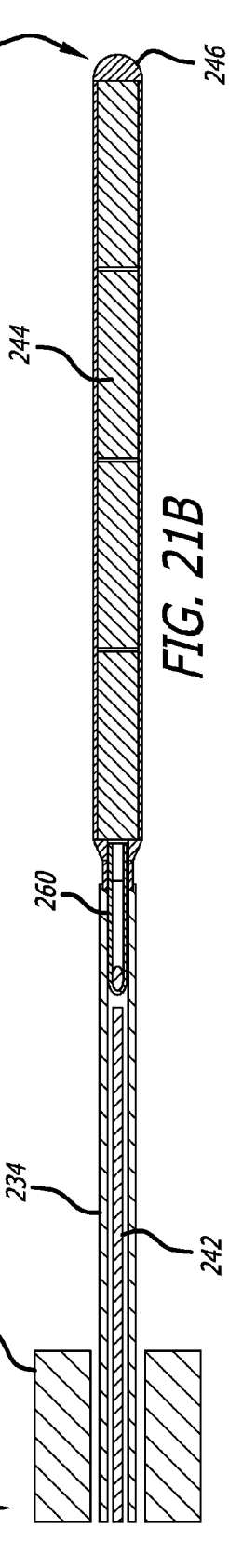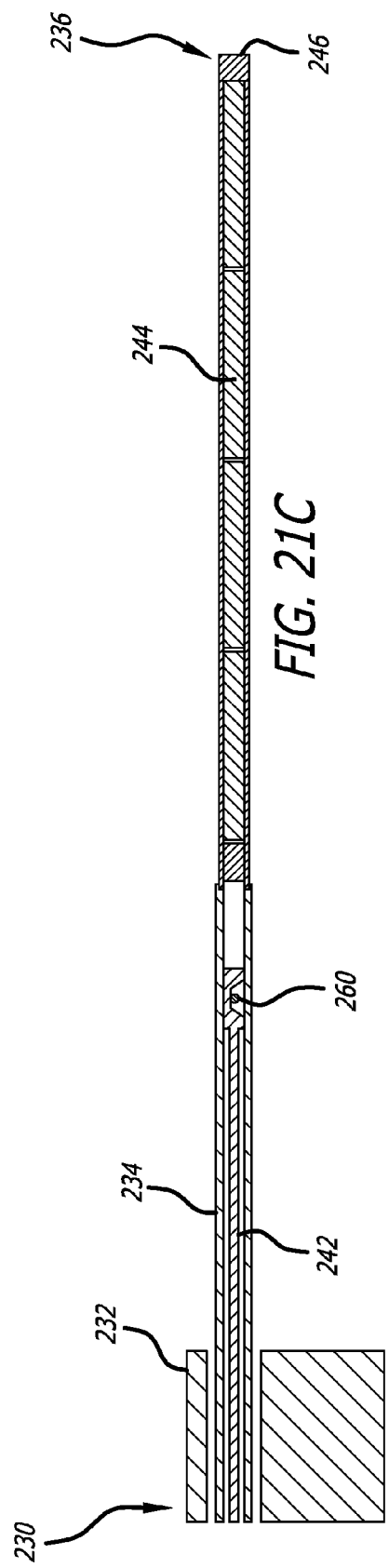

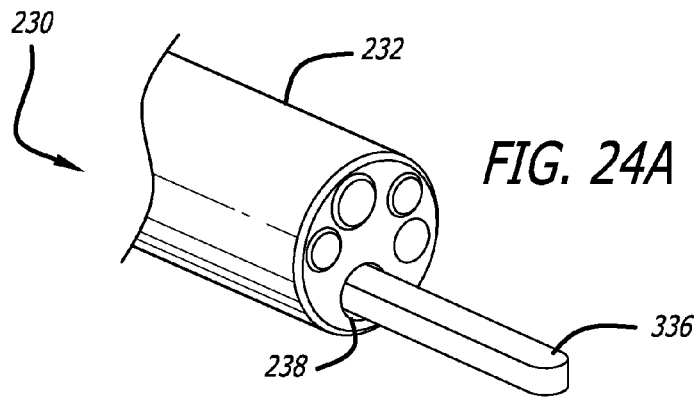
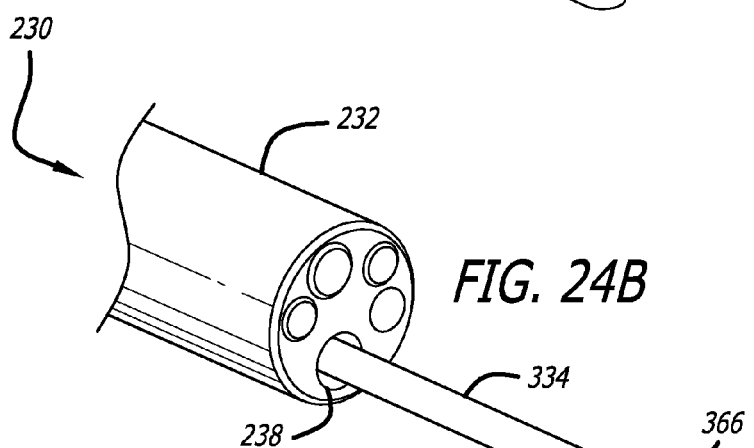
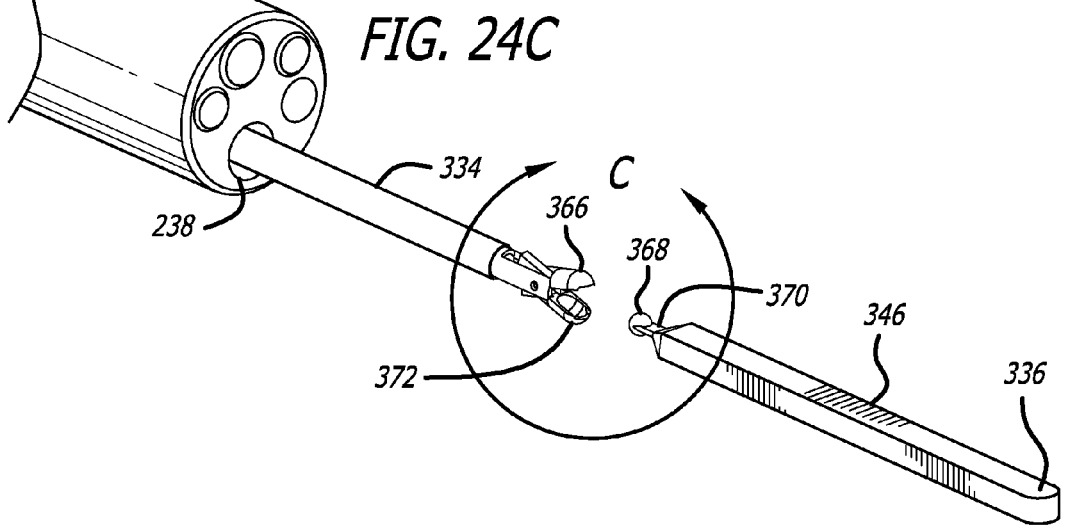

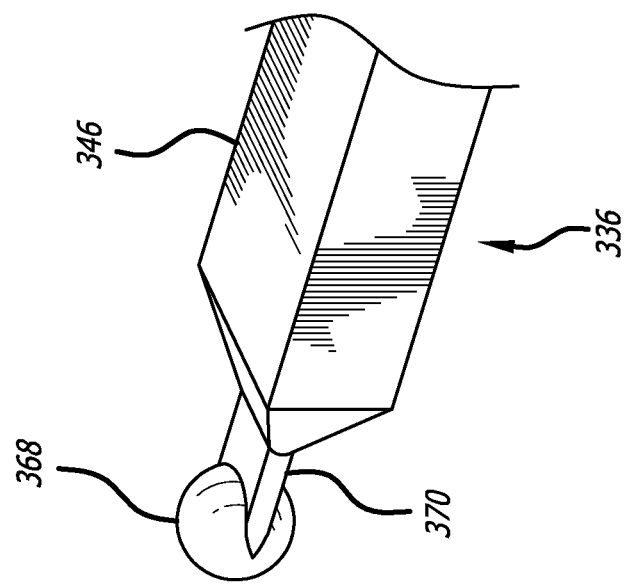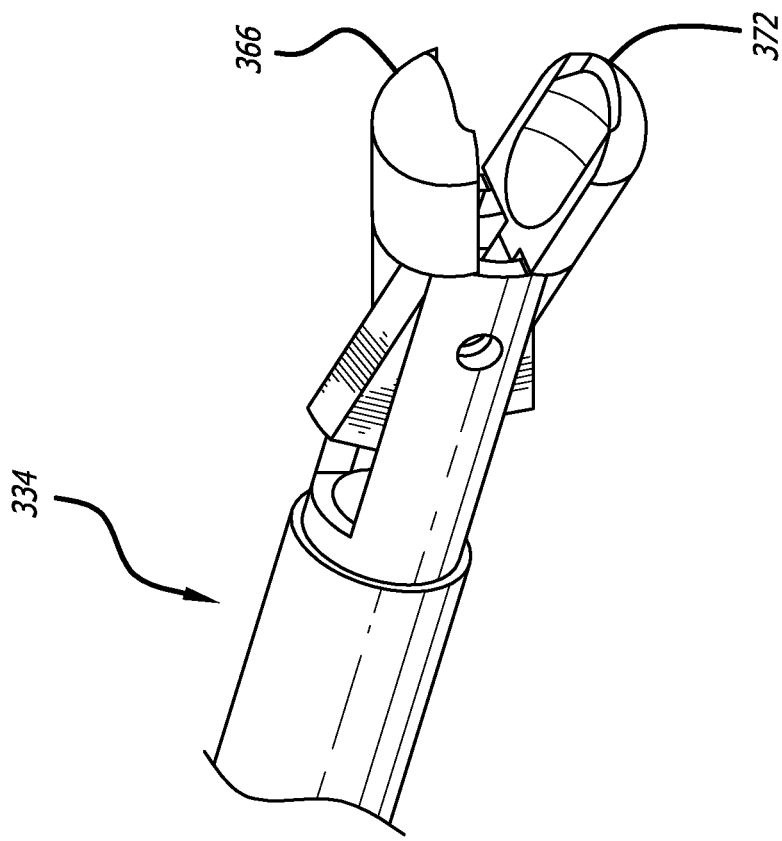
FIG. 24D

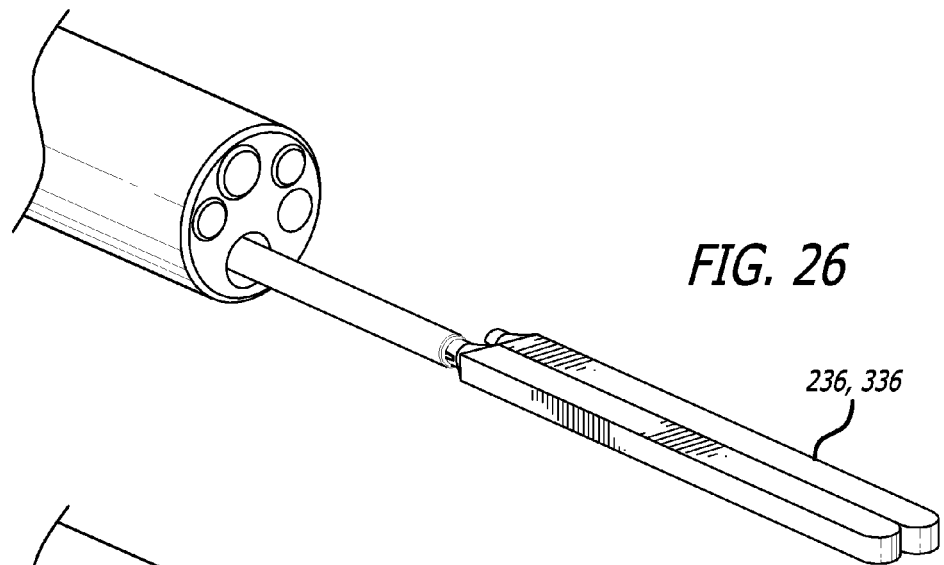
FIG. 26
236, 336
FIG. 27
236, 336
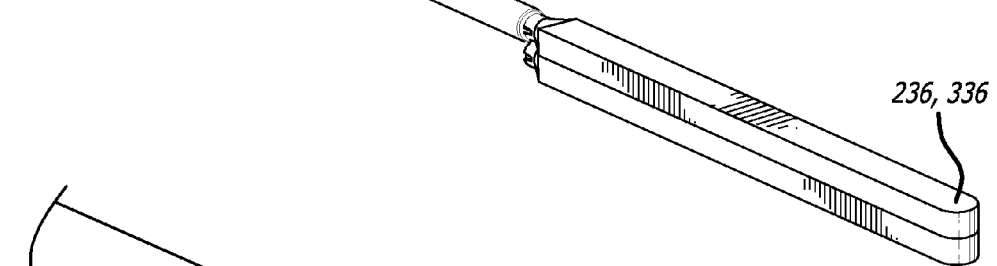
FIG. 28
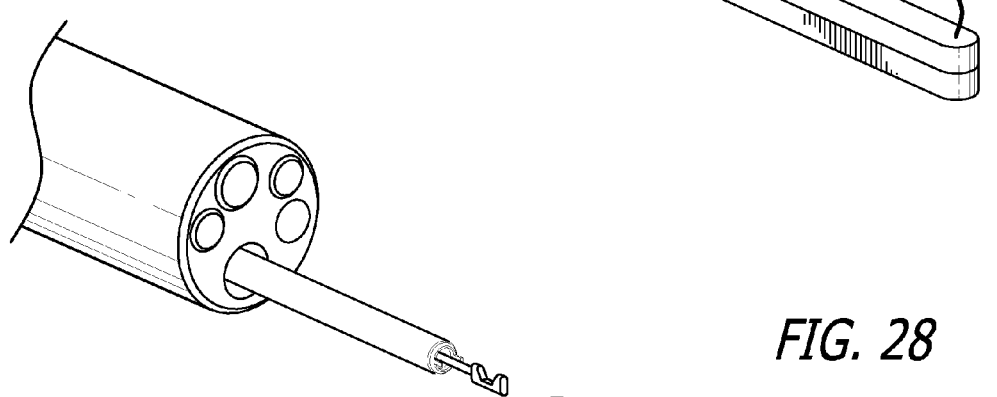
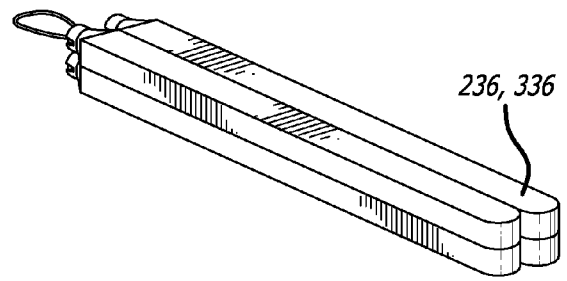
236, 336

INCISIONLESS GASTRIC BYPASS METHOD AND DEVICES

RELATED APPLICATIONS

This application is a divisional of U.S. patent application Ser. No. 12/837,392 filed Jul. 15, 2010 now abandoned entitled Incisionless Gastric Bypass Method And Devices, which claims priority to U.S. Provisional Application Ser. No. 61/226,225 filed Jul. 16, 2009 entitled Incisionless Gastric Bypass Method And Devices, and to U.S. Provisional Application Ser. No. 61/225,901 filed Jul. 15, 2009 entitled Incisionless Gastric Bypass Method & Devices, all of which are hereby incorporated in their entireties herein.

BACKGROUND OF THE INVENTION

The present invention relates generally to addressing problems related to the digestive system, particularly obesity and type II diabetes. Additionally, it is contemplated that the methods and devices of the present invention may be used in treating other digestive conditions such as benign or malignant obstructions of the stomach, small bowel and/or colon when clinically indicated; peptic ulcer disease; inflammatory bowel disease; adhesions; annular pancreas; duodenal, pancreatic, intestinal, or colonic primary malignancies; and secondary malignancies.

Obesity

According to the Center for Disease Control (CDC), sixty six percent of the United States population are overweight, and thirty two percent are obese, presenting an overwhelming health problem. From an economic standpoint, it is estimated that more than 100 billion dollars are spent on obesity and treating its major co-morbidities. This figure does not include psychological and social costs. Many health care experts consider obesity the largest health problem facing westernized societies and consider obesity an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon cancers. Despite these alarming facts, treatment options for obesity remain limited.

Treatment options include dietary modification, very low-calorie liquid diets, pharmaceutical agents, counseling, exercise programs and surgery. Diet and exercise plans often fail because most individuals do not have the discipline to adhere to such plans. When diet and exercise fail, many try dietary supplements and drugs or other ingestible preparations promoted as being capable of suppressing appetite or inducing satiety. In general, these techniques for treating compulsive overeating/obesity have tended to produce only a temporary effect. The individual usually becomes discouraged and/or depressed after the initial rate of weight loss plateaus and further weight loss becomes harder to achieve. The individual then typically reverts to the previous behavior of compulsive overeating.

Surgical procedures that restrict the size of the stomach and/or bypass parts of the intestine are the only remedies that provide lasting weight loss for the majority of morbidly obese individuals. Surgical procedures for morbid obesity are becoming more common based on long-term successful weight loss result.

Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found on the website of the American Society for Bariatric Surgery at http://www.asmbs.org, the contents of which are incorporated by reference herein in their entirety.

The surgeries which create malabsorption, such as the by-pass operations, although effective in weight reduction, involve permanent modification of the GI tract and have a risk of short and long term complication and even death.

Gastric bypass is the most common weight loss operation in the United States. This procedure reduces the size of the stomach and shortens the effective-length of intestine available for nutrient absorption. With gastric bypass many investigators have reported weight loss results that exceed 70% of excess weight. However, this efficacy does not come without complication. The accepted mortality of the procedure is 1 in 200. Additionally, because various sections of the intestine are responsible for absorbing various nutrients from the chyme being digested, bypassing sections of the intestine can result in an inability of the modified digestive tract to benefit from certain nutrients. In certain cases, this results in conditions such as anemia and must be treated with high doses of vitamin or nutrient supplements.

Diabetes

According to the National Institute of Diabetes and Digestive and Kidney Diseases (NIDDK) an estimated 20.8 million people in the United States, 7.0 percent of the population, have diabetes, a serious, lifelong condition. Of those, 14.6 million have been diagnosed, and 6.2 million have not yet been diagnosed. In 2005, about 1.5 million people aged 20 or older were diagnosed with diabetes. According to the American Diabetes Association, the total annual economic cost of diabetes in 2002 was estimated to be $132 billion.

Diabetes is a set of related diseases in which the body cannot regulate the amount of sugar (glucose) in the blood. Glucose in the blood provides the body with energy. In a healthy person, the blood glucose level is regulated by several hormones including insulin, glucagons, and epinephrine. Insulin is produced by the pancreas, a small organ near the stomach that also secretes important enzymes that help in the digestion of food. Insulin allows glucose to move from the blood into the liver, muscle, and fat cells, where it is used for fuel.

At least 90% of patients with diabetes have Type 2 diabetes wherein the pancreas secretes insulin but the body is partially or completely unable to use the insulin. This is sometimes referred to as insulin resistance. The body tries to overcome this resistance by secreting more and more insulin. People with insulin resistance develop Type 2 diabetes when they do not continue to secrete enough insulin to cope with the higher demands.

Recently, evidence for reduction of complications of type 2 diabetes with tight control of hyperglycemia has been reported, but current therapies, including diet, exercise, behavior modification, oral hypoglycemic agents, and insulin, rarely return patients to euglycemia.

For reasons not completely known, the majority of patients who undergo gastric bypass surgery experience resolution of Type 2 diabetes and enjoy normal blood glucose and glycosylated hemoglobin levels with discontinuation of all diabetes-related medications. One hypothesis, that has been proposed, is that diabetes control results from the expedited delivery of nutrient-rich chyme (partially digested food) to the distal intestines, enhancing a physiologic signal that improves glucose metabolism, the so called "hindgut hypothesis". However, because gastric bypass surgery is considered a relatively high-risk major surgery, it is not used to treat Type 2 diabetes.

OBJECTS AND SUMMARY OF THE INVENTION

The methods and devices of the present invention are primarily directed to a minimally invasive, endoscopic solution for treating patients with obesity and/or Type 2 diabetes. The methods and devices can also be of benefit in laparoscopic and open surgical procedures. The solution is simple, user-friendly, reversible, and does not require a permanent implant. When the procedure is performed endoscopically, the need for abdominal incisions is eliminated. Thus, the procedure has the potential of being performed outside of the operating room, potentially in an endoscopy suite.

One aspect of the present invention treats the aforementioned conditions by creating a partial bypass of a portion of the small intestines. Preferably, an anastomosis is created between the distal portion of the second section and/or third section of the duodenum and the ileum or colon. Using anatomical landmarks as reference, the anastomosis should preferably be positioned in the duodenum distal to the hepatopancreatic ampulla where the common bile and main pancreatic duct empty into the duodenum and proximal to the point where the superior mesenteric artery and vein cross over the duodenum.

This solution creates an alternative pathway for chyme. A portion of the nutrients will bypass a portion of the small intestines and thus not be absorbed (controlled absorption). The amount of bypass is controlled by the size of the anastomosis. The physician is thus able to vary the size of the anastomosis both at the time of the procedure and during subsequent follow-up procedures. The anastomosis also provides a bypass for nutrient-rich chyme to enter the ileum or colon. This is thought to have the effect of triggering early satiety as well as improving glucose metabolism. A potential candidate mediator of this effect is glucagon-like peptide 1 (GLP-1). This incretin hormone is secreted by cells in the distal bowel in response to nutrients, which stimulates insulin secretion.

Another aspect of the present invention provides a method by which an endoscope is inserted orally and advanced through the upper GI track and then into the duodenum. Another endoscope is inserted anally and advanced into the colon or ileum. The normal anatomy in a human is such that the second and third sections of the duodenum are in close proximity with portions of the ileum and colon. If either structure is illuminated from within, it can readily be seen from the other. For example, if the duodenum is illuminated, the light can be seen with an endoscope in the ileum or colon and the ileum or colon can then be gently maneuvered such that it is touching the duodenum. The ileum or colon can also be positioned by visualizing the endoscopes using fluoroscopic imaging and maneuvering the endoscope within the ileum or colon to close proximity of the endoscope in the duodenum.

Once intimate contact has been confirmed between the duodenum and the ileum or colon, magnets that have been pre-attached to the endoscope are coupled. In another embodiment of the invention magnets are passed through the working channel of the endoscope rather than pre-attached. Once the magnets have been magnetically coupled and alignment is verified utilizing endoscopic and/or fluoroscopic imaging, they are released from the endoscopes. The two coupled magnets create intimate contact between the serosal surfaces of the two vessels. During the healing period the tissue between the magnets is compressed and becomes necrotic. The tissue near the outside of the anastomosis device is compressed at a lower force. This tissue forms a region or ring of healed tissue. After a few weeks the necrotic tissue, along with the magnetic implants detach and are expelled. There is no flow between vessels during the healing period. Everything flows through the natural distal duodenum and thus there is no risk of obstructing flow. Human serosal tissue that is placed in intimate contact has been shown to heal within 7 days.

Patients can be tracked and if absorption needs to be further limited a follow up procedure can be performed to create additional anastomosis in the same or other locations or make the anastomosis larger. Likewise, if the anastomosis is too large, it may be modified by closing a portion of the anastomosis with an endoluminal suturing, stapling, or clip device. The procedure may be completely reversed by closing the entire anastomoisis with such devices.

BRIEF DESCRIPTION OF THE DRAWINGS

FIG. 11b is a perspective view of the device of FIG. 11a being released from the delivery device of FIG. 11a;

FIG. 12b is a section view taken along lines A-A of FIG. 12a;

FIG. 16b is a perspective view of the device of FIG. 16a being advanced from a distal end of the delivery device of FIG. 16a;

FIG. 16c is a perspective view of the device of FIG. 16a being released from the delivery device of FIG. 16a;

FIG. 17b is a section view taken along lines B-B of FIG. 17a;

FIG. 18a is a perspective view of an embodiment of a device of the present invention attached to an embodiment of a delivery device of the present invention;

FIG. 18b is a perspective view of the device of FIG. 18a being advanced from a distal end of the delivery device of FIG. 18a;

FIG. 18c is a perspective view of the device of FIG. 18a being released from the delivery device of FIG. 18a;

FIG. 19 is a detail view of area A of FIG. 18b;

FIG. 20 is a detail view of area B of FIG. 18c;

FIG. 21a is an end view of an embodiment of a device of the present invention attached to an embodiment of a delivery device of the present invention;

FIG. 21b is a section view taken along lines C-C of FIG. 21a;

FIG. 21c is a section view taken along lines D-D of FIG. 21a;

FIG. 23b is a perspective view of the device of FIG. 23a being released from the delivery device of FIG. 23a;

FIG. 24a is a perspective view of an embodiment of a device of the present invention attached to an embodiment of a delivery device of the present invention;

FIG. 24b is a perspective view of the device of FIG. 24a being advanced from a distal end of the delivery device of FIG. 24a;

FIG. 24c is a perspective view of the device of FIG. 24a being released from the delivery device of FIG. 24a;

FIG. 24d is a detail view of area C of FIG. 24c;

FIG. 26 is a perspective view of an embodiment of a delivery device of the present invention being used to deliver an arrangement of two devices according to an embodiment of the present invention;

FIG. 27 is a perspective view of an embodiment of a delivery device of the present invention being used to deliver an arrangement of two devices according to an embodiment of the present invention;

FIG. 28 is a perspective view of an embodiment of a delivery device of the present invention being used to deliver an arrangement of four devices according to an embodiment of the present invention;

FIG. 30b is a perspective view of the device of FIG. 30a being advanced from a distal end of the delivery device of FIG. 30a;

FIG. 30c is a perspective view of the device of FIG. 30a being released from the delivery device of FIG. 30a;

FIG. 31b is a perspective view of the device of FIG. 31a being advanced from a distal end of the delivery device of FIG. 31a;

FIG. 31c is a perspective view of the device of FIG. 31a being released from the delivery device of FIG. 31a;

DETAILED DESCRIPTION OF THE EMBODIMENTS

The invention provides for the method and device apparatus to create a partial bypass between the duodenum and ileum or duodenum and colon utilizing a completely incisionless endoscopic method using both the mouth and anus as natural pathways for gaining access to the preferred anastomosis location. An important aspect of the invention is that the anastomosis is created between naturally adjacent or close proximity sections of the duodenum and ileum or duodenum and colon, therefore allowing a means for a totally incisionless procedure. The invention generally involves inserting a first endoscopic delivery device orally into the duodenum. A similar second endoscopic delivery device is inserted anally into the colon or the ileum to a position where the tracts of the ileum or colon naturally lie adjacent or in close proximity to the duodenum. Having been pre-assembled at the distal tip of the endoscopic delivery device or advanced through a channel of the endoscope or overtube, the magnetic implants are subsequently aligned and magnetically coupled. The implant devices are magnetically attracted to each other (one or both being magnets) and are aligned to one another using visual and/or fluoroscopic guidance and released from their respective deployment devices. The magnetic implants apply force to the vessel walls trapped between them and pressure necrosis preferably results within a few weeks. The circumferential tissue near the edge of the magnetic devices is of lower pressure and creates a healed continuous region of tissue between the vessels. After an appropriate period of time, the coupled magnetic devices and compressed necrotic tissue detach from the surrounding tissue therefore creating an anastomosis. Subsequently, the magnetic implants pass through the digestive tract leaving no permanent implant in the body. A first series of device embodiments of the invention illustrate using magnetic implants that are pre-assembled to the distal tip of the endoscope. A second series of embodiments of the invention illustrates using magnetic implants that are advanced through the working channel of an endoscope instead of pre-assembled at the distal tip. A third series of embodiments illustrates releasably attaching the magnetic devices to an overtube that surrounds the endoscope as well as advancing the devices through a lumen within the wall of an overtube.

Figure 1:
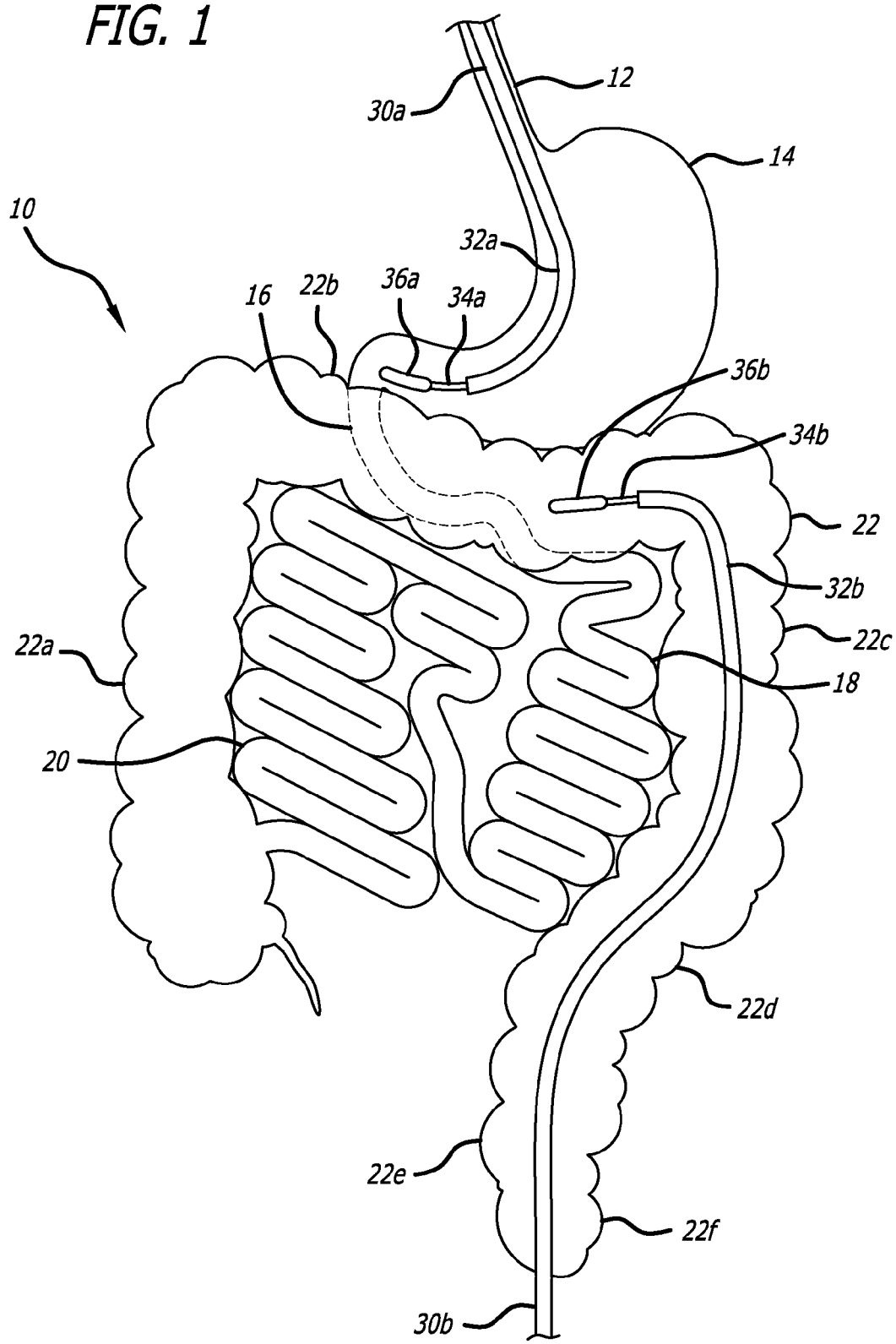
FIGS. 1-5 are views of the digestive system showing a progression of steps of an embodiment of a method of the present invention for creating a duodenum to colon anastomosis.

As shown in FIG. 1, the digestive tract 10 includes the esophagus 12, which empties into the stomach 14. Distal to the stomach is the small intestine, which is comprised of the duodenum 16, jejunum 18, and ileum 20 sections. The ileum 20 empties into a part of the colon 22 called the cecum. The colon generally consists of five main segments: ascending 22a, transverse 22b, descending 22c, sigmoid 22d, and rectum 22e.

Figure 6:
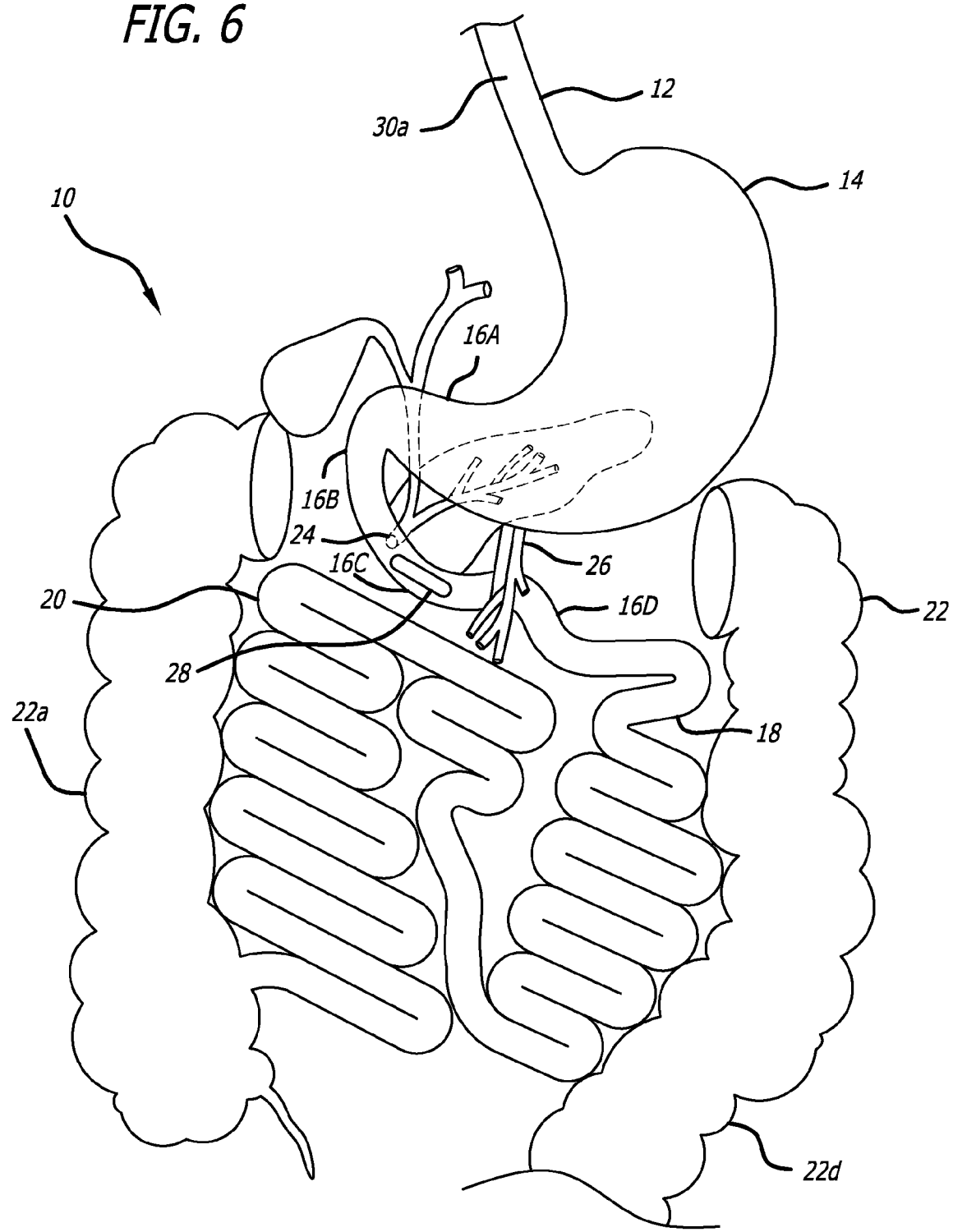
FIG. 6 is a partial view of the digestive system with an anastomosis formed by an embodiment of a method of the present invention.
Figure 7:
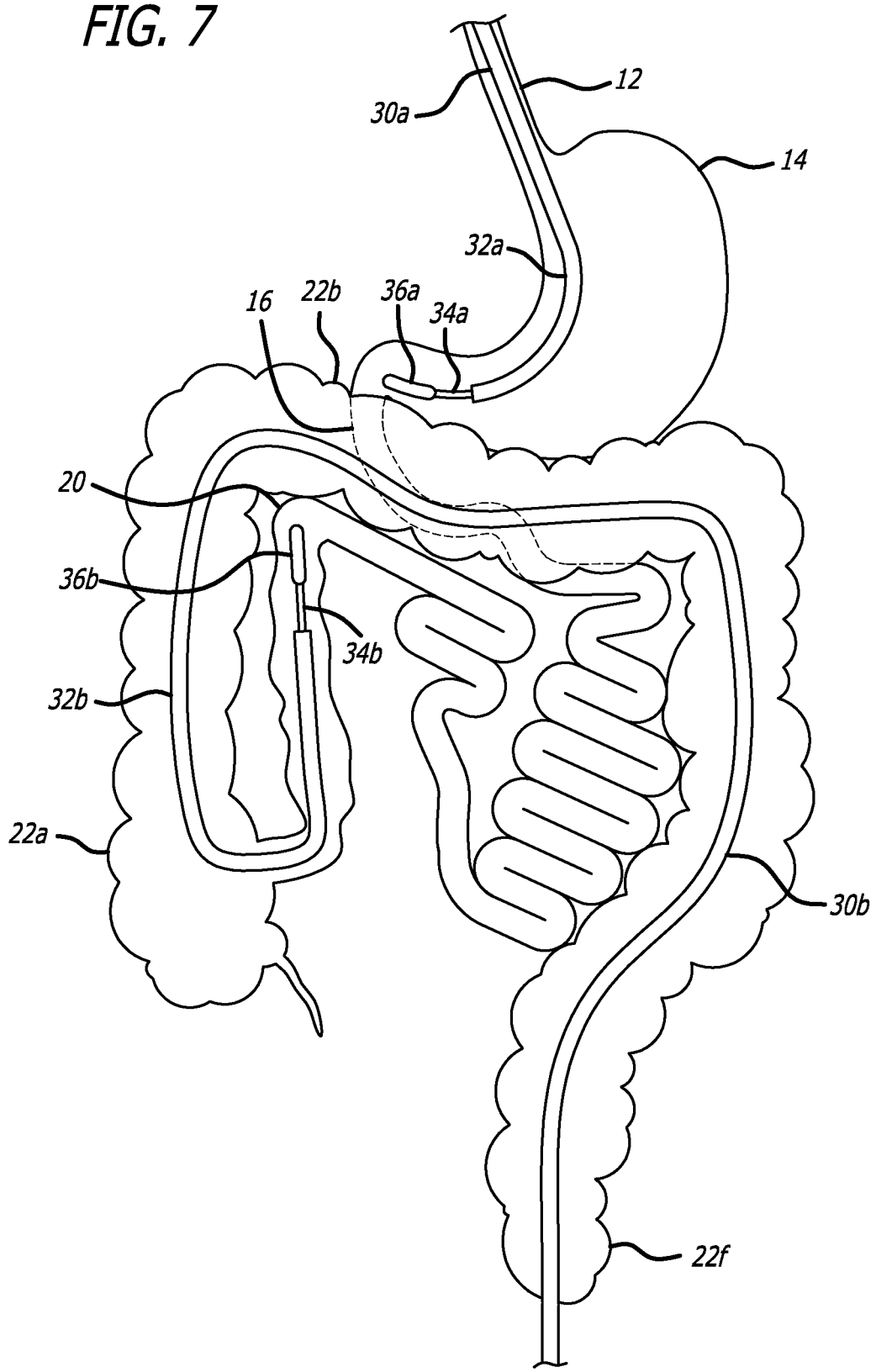
FIGS. 7-10 are views of the digestive system showing a progression of steps of an embodiment of a method of the present invention for creating a partial bypass with a side-to-side anastomosis between the duodenum and ileum.

FIG. 6 shows the various segments of the duodenum and anatomical landmarks within and around the duodenum. The duodenum consists of four segments: superior 16a, descending 16b, horizontal 16c, and ascending 16d. In this figure, a section of the transverse colon has been removed to view the anatomical landmarks near the duodenum more clearly. Generally, the common bile and pancreatic ducts combine into the hepatopancreatic ampulla 24 which empties into the descending duodenum 16b approximately two-thirds along its length. The superior mesenteric artery and vein 26 cross the horizontal duodenum segment 16c at its distal end.

Although an anastomosis could be made anywhere in the duodenum to the ileum or colon, the preferred duodenal location for the anastomosis 28 is in the distal third of the descending segment 16b and/or the horizontal segment 16c of the duodenum, provided that the anastomosis is distal to the hepatopancreatic ampulla 24 and proximal of the superior mesenteric artery and vein 26. Creating the anastomosis distal to the common bile and pancreatic ducts will allow their contents to flow in the newly created partial bypass as well as in the original natural tract. Positioning the anastomosis proximal of the superior mesenteric artery and vein provides many benefits: 1) access is easier than going more distal, 2) the malabsorptive effect will be enhanced from bypassing the duodenum more proximally, 3) the position is ideal for connecting the duodenum to naturally adjacent segments of the colon and ileum, and 4) connecting proximal of the superior mesenteric artery and vein avoids potential complications of placing devices on or directly adjacent the wall of the superior mesenteric artery and vein.

Referring to FIGS. 1 and 6 for the duodenum to colon side-to-side anastomosis, the invention takes into account that the transverse colon 22b naturally lies on top of (superior) the preferred location in the duodenum 28 as described above, in which, the superior wall of the duodenum is adjacent the posterior wall of the transverse colon 22b. Creating an anastomosis between naturally adjacent tracts simplifies the procedure of accessing the anastomosis sites and aligning the anastomosis devices into correct position. This is especially evident for a duodenum to transverse colon anastomosis as it is of common practice and skill level for endoscopists to access these locations in the digestive tract. Although advanced access tools such as single or double balloon enteroscopy may be used, this anastomosis location allows the use of standard endoscopic devices to access the duodenum and transverse colon.

A first endoscopic delivery device 30a is inserted orally and advanced through the esophagus 12, stomach 14, and into the duodenum 16. The endoscopic delivery device 30a consists of a pre-assembled endoscope 32a, delivery catheter 34a, and magnetic implant 36a. The magnetic implant 36a is releasably attached to the distal tip of the delivery catheter 34a which has been loaded into a working channel of the endoscope 32a.

Similarly, a second endoscopic delivery device 30b is inserted through the anus 22f and advanced into the transverse colon 22b. In similar fashion, the endoscopic delivery device 30b consists of a pre-assembled endoscope 32b, delivery catheter 34b, and magnetic implant 36b. The magnetic implant 32b is releasably attached to the distal tip of the delivery catheter 34b which has been loaded into a working channel of the endoscope 32a.

Figure 2:
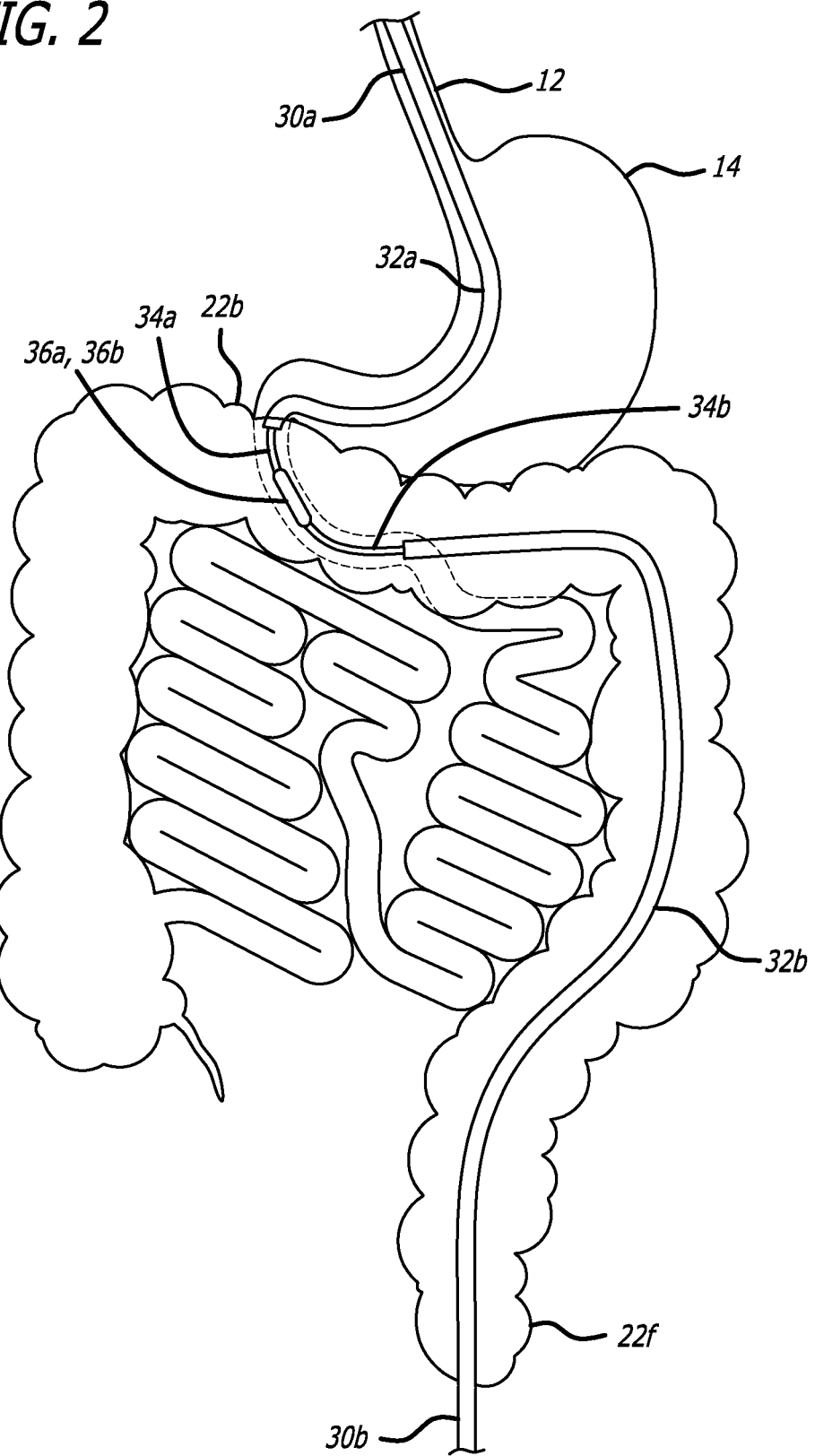

Once the first 30a and second 30b endoscopic delivery devices are roughly positioned into the duodenum 16 and transverse colon 22b as shown in FIG. 1, the operator should confirm that the endoscopes are in adjacent vessels with close proximity. This may be accomplished by visualizing the light source emitted from the first endoscope by the second endoscope. For example, the light source emitted by the endoscope 32a in the duodenum 16 should be easily viewed by the endoscope 32b in the transverse colon 22b and vise-versa. Additionally, or instead of the light source, the position of the first endoscope to the second may be verified by visualizing the first endoscope touching and moving the wall of the vessel of the second endoscope. For example, the first endoscope 32a in the duodenum 16 may be articulated to touch and displace the wall of both the duodenum and the adjacent wall of the transverse colon. The second endoscope in the transverse colon 22b would view the resulting wall motion to confirm the proximity of the first endoscope in the duodenum. An additional and preferred method of confirming that the endoscopes are in adjacent vessels of close proximity is to use fluoroscopy to confirm the position and aid in guiding the magnetic implants into their final coupled position. For example, if the distal end of the roughly positioned endoscopic delivery device 30a in the duodenum 16 is not in close proximity and adjacent to the distal end of the endoscopic delivery device 30b in the transverse colon 22b, fluoroscopy may be used to articulate the distal tip of the endoscopic delivery devices and their respective vessels into final position. This is accomplished by manipulating and articulating the endoscopes 32a and 32b, the delivery catheters 34a and 34b, and/or the magnetic implant 36a and 36b. The delivery catheter 34 is designed to move axially within the working channel of the endoscope 32 and may also be designed so that its distal tip may articulate the attached magnetic implant 36. The magnetic implant 36 may be positioned axially or radially by advancing or rotating the delivery catheter 34 relative to the endoscope 32. Contrast may be injected into the duodenum 16 and transverse colon 22b during fluoroscopy to visualize the vessels and help bring them into proximity to one another by articulating and manipulating the devices. Once brought into close proximity, the magnetic implants will couple and self align as shown in FIG. 2. Once coupled, the magnetic implant in the duodenum should be visually inspected to make sure it is in the preferred position 28 as described previously and shown in FIG. 6. Additionally, fluoroscopy may be used to verify that the magnetic implants are properly oriented and contrast may be injected to show that the vessels remain adjacent and are not adversely twisted. If the magnetic implants are not properly aligned or the vessel wall has been adversely deformed, the magnetic implants may be pulled apart and repositioned using the same techniques as described above. Once the operator is satisfied with the positioning of the magnetic implants and vessel geometry, the coupled magnetic implants 36a and 36b are released from their respective delivery catheters 34a and 34b and the endoscopic delivery devices are removed from the body. If the implants need to be repositioned or removed after release, it is preferable that the implants could be easily recaptured using the same endoscopic delivery devices.

Figure 3:
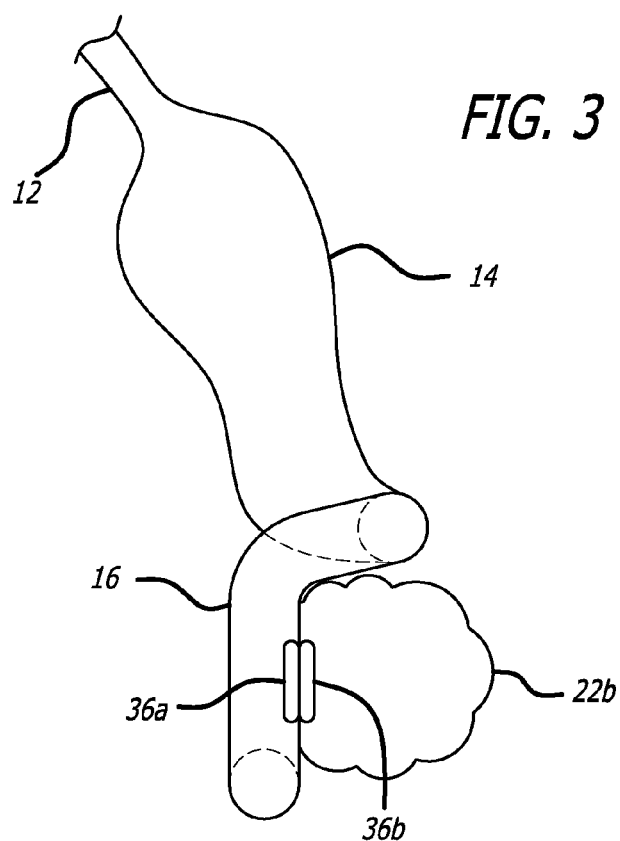
Figure 4:
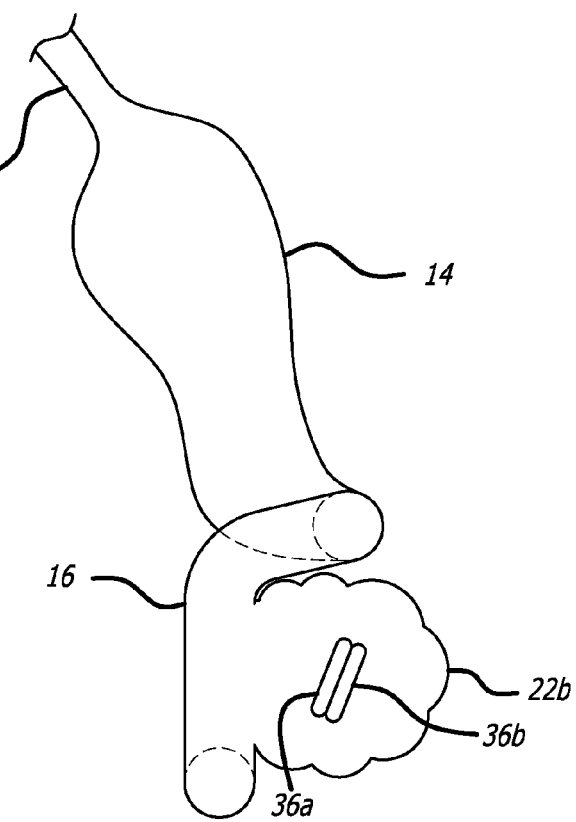
Figure 5:
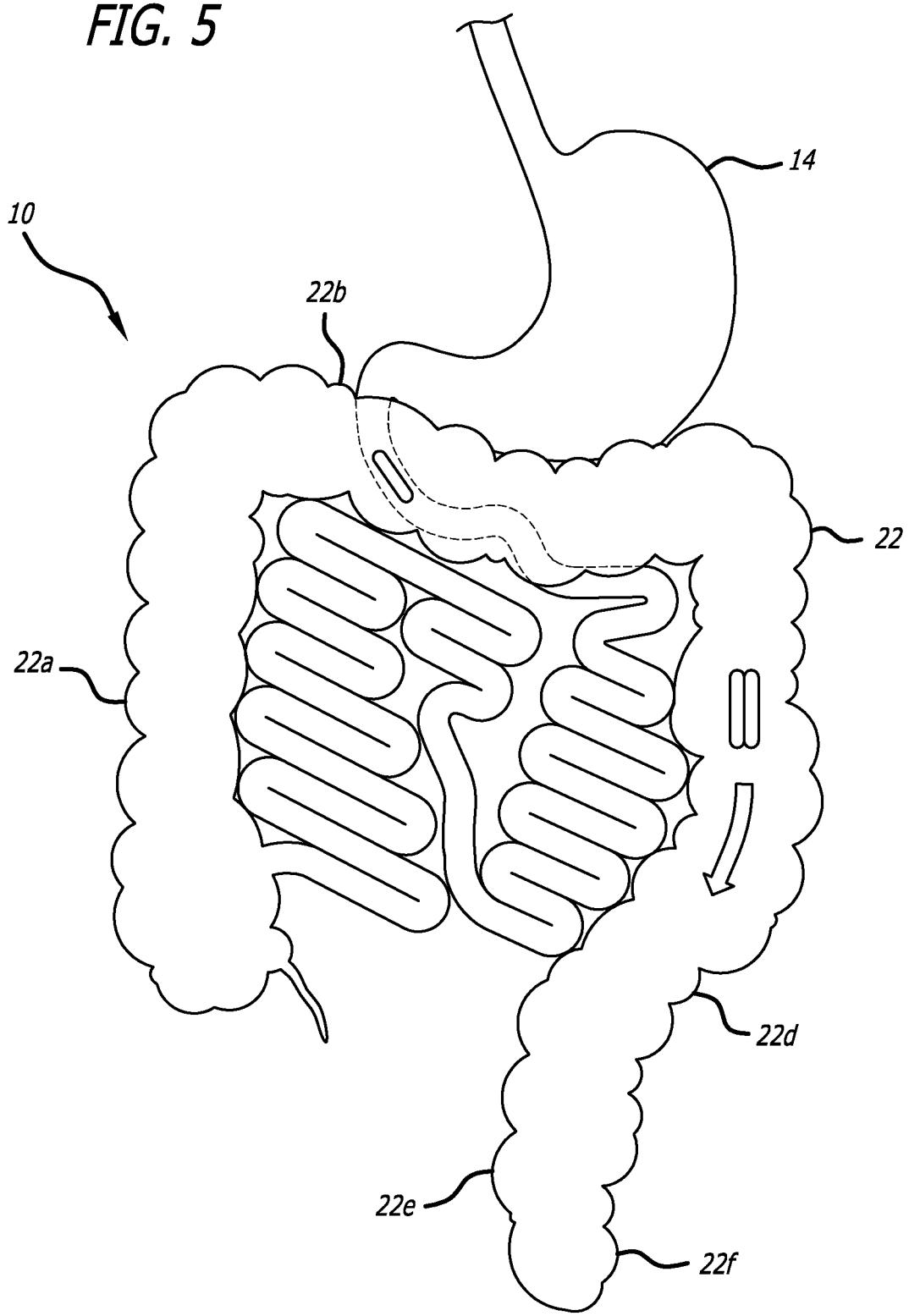

FIG. 3 shows a lateral view of FIG. 2 of the coupled magnetic implants 36a and 36b after they have been released from the delivery catheters 34a and 34b. The magnetic implants 36a and 36b compress the duodenal and colon wall between them which results in ischemic pressure necrosis of the tissue trapped between them. The surrounding circumferential tissue is compressed at a lower force and results in a healed continuous region or ring of tissue between the vessels around the magnetic implants. After an appropriate period of time, the coupled magnetic implants and compressed necrotic tissue detach from the surrounding tissue and therefore create an anastomosis. Once detached, the implants pass through the digestive tract, leaving no device in the body. FIG. 4 illustrates the anastomosis after the magnetic implants have detached from the surrounding tissue and are about to start their journey out of the digestive tract. FIG. 5 shows the preferable path the magnetic implants take to be eliminated from the digestive tract. No permanent implant is left in the body. Although not ideal, the magnetic implants may start their journey by traveling down the duodenum instead of the colon side of the anastomosis. This may take longer for the implants to exit the body as they are taking a longer pathway. It is also contemplated that if they initially started down the duodenum (long path) that once they reach the colon side of the anastomosis that they could pass through the anastomosis and travel down the duodenum side a second time.

Notice in FIG. 4 and FIG. 5 the resulting anastomosis creates a partial bypass where chyme may take one of two paths: 1) the original natural path through the duodenum and on to the jejunum or 2) the new path created with the anastomosis to the transverse colon 22b. It is the object of this invention to leave the original natural path in place so that chyme, bile, and other digestive juices may travel down both paths. Chyme that takes the new path will bypass a portion of the small intestines and therefore not be absorbed. The ratio of chyme going through the new path may be dependent on the size of the anastomosis relative to the original vessel size. The size of the anastomosis may be tailored by the physician at the time of the procedure and during subsequent follow-up procedures. For example, if the first anastomosis was not large enough to create the desired effect, the physician could enlarge the first anastomosis with another device or create a second anastomosis preferably after the first anastomosis device had exited the body. Alternatively, if the first anastomosis was too large or the procedure needed to be reversed, the physician could partially or completely close the anastomosis with a transluminal suturing, stapling, or clip device. The anastomosis also provides a bypass for nutrient-rich chyme to enter the ileum or colon. This is thought to have the effect of triggering early satiety as well as improving glucose metabolism. A potential candidate mediator of this effect is glucagon-like peptide 1 (GLP-1). This incretin hormone is secreted by cells in the distal bowel in response to nutrients, which stimulates insulin secretion.

The present invention also contemplates a duodenum to ileum anastomosis, taking into account that a portion of the ileum 20 naturally lies adjacent or in close proximity to the preferred location in the duodenum 28 as described above. Although the ileum is a more difficult region to access than the transverse colon from the large intestines, using adjacent tracts will simplify locating and aligning the duodenum and ileum vessels and magnetic anastomosis devices to one another. Advanced access tools such as single and double balloon enteroscopy devices may be used to access this location. It is preferable that an anastomosis device and delivery system work in conjunction with advanced access tools and techniques.

It should also be noted that use of the term "adjacent to" or "in close proximity to" as used herein accounts for anatomical variations, which may account for a separation of up to a few inches. It is well within the scope of the present invention to use the distal ends of the probes/endoscopes to move the digestive tract slightly to establish a magnetic connection. Notably, unlike prior art references that puncture the digestive tract with additional probes in order to manipulate anatomy while establishing connections (see e.g. U.S. Patent Publication 2008/0208224 to Surti et al.), the devices and methods of the present invention have been found to easily manipulate portions of the digestive tract significant distances by simply advancing the probes/endoscopes into the lumen walls of the bowels. Hence, it is contemplated that the present invention encompasses doing so, preferably without making a single incision or puncture through patient tissue.

FIGS. 7-10 show in stepwise fashion an incisionless method for creating a partial bypass with a side-to-side anastomosis between the duodenum 16 and ileum 20. A first endoscopic delivery device 30a is inserted orally and advanced through the esophagus 12, stomach 14, and into the duodenum 16. The endoscopic delivery device 30a consists of a pre-assembled endoscope 32a, delivery catheter 34a, and magnetic implant 36a. The magnetic implant 36a is releasably attached to the distal tip of the delivery catheter 34a which has been assembled into a working channel of the endoscope 32a.

A second endoscopic delivery device 30b is inserted through the anus 22f, advanced into the ascending colon 22a, and further advanced into the ileum 20. In similar fashion, the endoscopic delivery device 30b consists of a pre-assembled endoscope 32b, delivery catheter 34b, and magnetic implant 36b. The magnetic implant 36b is releasably attached to the distal tip of the delivery catheter 34b which has been loaded into a working channel of the endoscope 32b.

Figure 8:
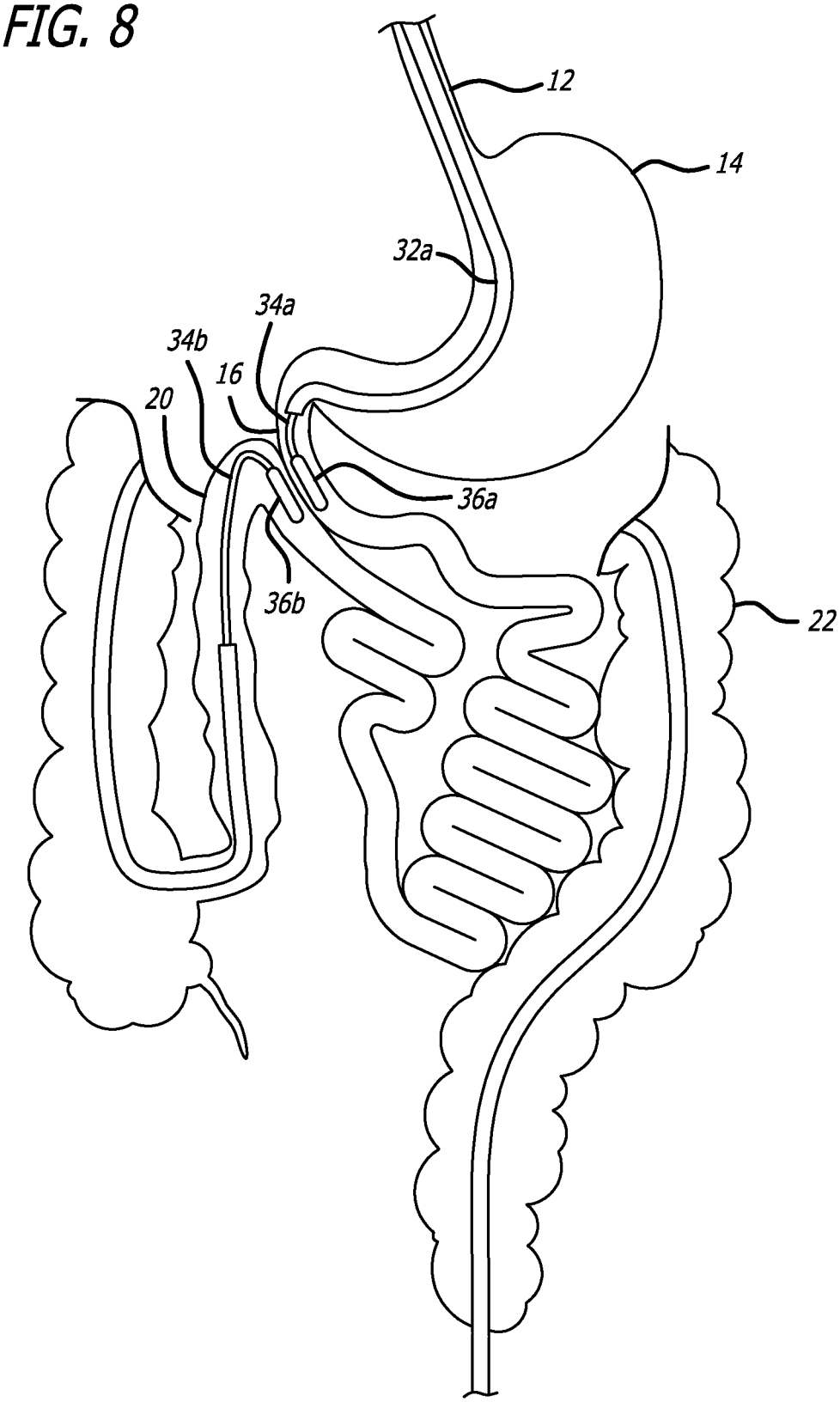
Figure 9:
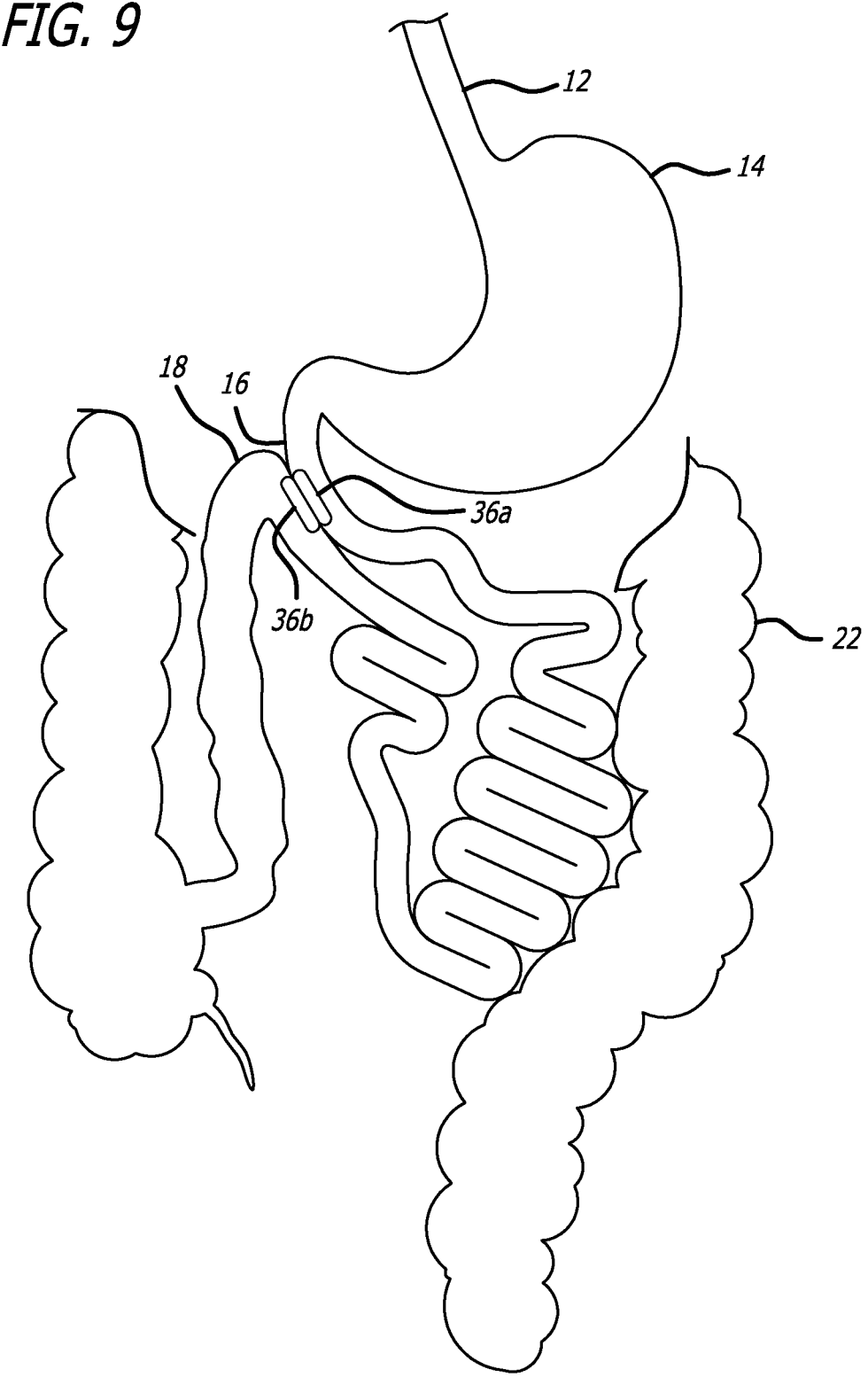
Figure 10:
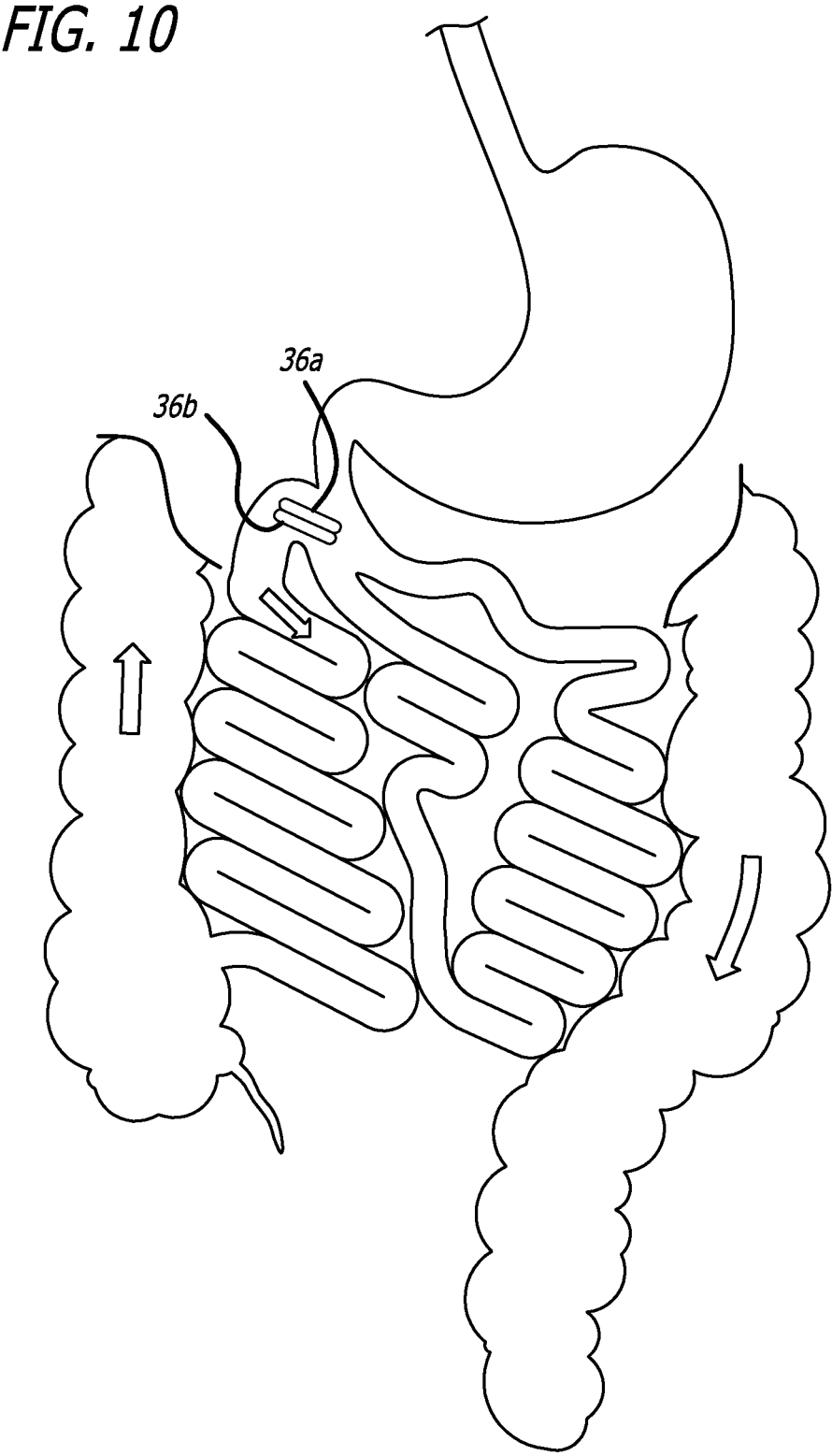

The rough position of the magnetic implants 36a and 36b and vessels 16 and 20 are respectively confirmed and finely positioned using the same method as described previously. FIG. 8 shows the magnetic implants 36a and 36b coupled together after the vessels are positioned appropriately according to the previously described method. FIG. 9 shows the magnetic implants 36a and 36b after they have been released from the delivery catheters 34a and 34b. The magnetic implants apply force for a period of time sufficient for pressure necrosis to create the anastomosis. FIG. 10 illustrates the anastomosis after the magnetic implants 36a and 36b have detached from the surrounding tissue and are about to start their journey out of the digestive tract. FIG. 10 also shows the preferable path the magnetic implants take to be eliminated from the digestive tract. No permanent implant is left in the body. Although not ideal, the magnetic devices may start their journey by traveling down the duodenum instead of the ileum side of the anastomosis. This may take longer for the implants to exit the body as they are taking a longer pathway. It is also contemplated that if they initially started down the duodenum (long path) that once they reach the ileum side of the anastomosis that they could pass through the anastomosis and travel down the duodenum a second time. As described previously, the anastomosis size may be subsequently altered in a second procedure.

The devices used to deploy and create the anastomoses in the previously described methods for creating a partial bypass between the duodenum and transverse colon and duodenum to ileum will now be explained in greater detail. For simplicity, most of the figures will only show one device in each figure, however, it is assumed that a second, preferably nearly identical, device will be needed to create the anastomosis as shown in the methods previously described for creating a duodenum to ileum or colon anastomosis. The endoscope used in the embodiments may be different if deploying a magnetic implant in the upper gastrointestinal tract such as the duodenum than an implant deployed in the ileum or colon. For example, a gastroscope may be used with the devices delivered into the duodenum and a colonoscope may be used with devices delivered into the colon or ileum. Also, the magnet in the second device will be assembled in the opposite polarity from the first so that the first and second implant attract instead of repel each other. Although not an all inclusive list, many embodiments will be described so that those skilled in the art will appreciate that variations upon these embodiments are within the spirit of the invention.

Figure 11A:
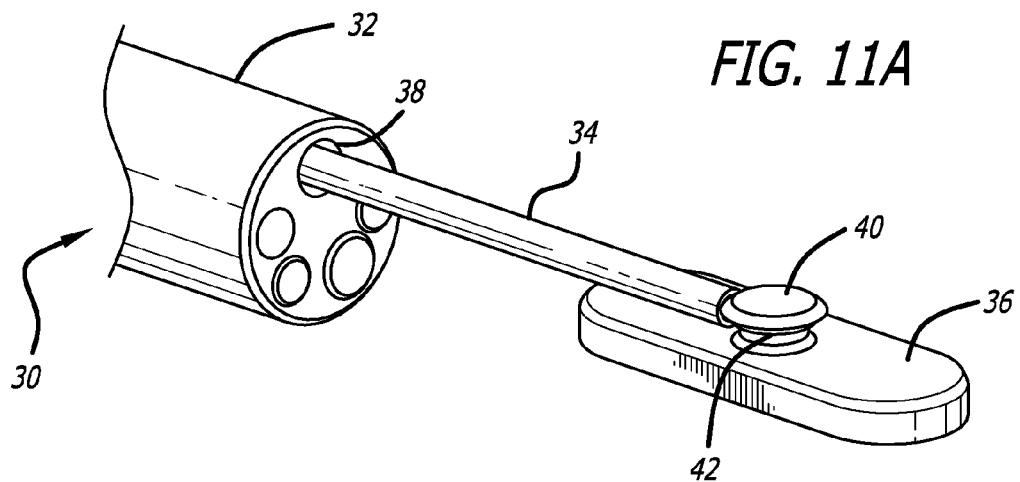
FIG. 11a is a perspective view of an embodiment of a device of the present invention attached to an embodiment of a delivery device of the present invention.

FIG. 11a shows an embodiment of a device useable to carry out the methods described previously, in that, the endoscopic delivery device 30 consists of a pre-assembled endoscope 32, delivery catheter 34, and implant 36. The delivery catheter 34 is loaded into the working channel 38 of the endoscope 32 and the implant 36 is releasably attached to the distal end of the delivery catheter 34 using a snare 42 that is wrapped around a knob feature 40 integral to the magnetic implant 36. The implant 36 is docked onto the delivery catheter 34 by applying tension to the snare wire 42 relative to the delivery catheter and locking the wire relative to the delivery catheter in a handle set that would be positioned at the proximal end of the delivery catheter.

The implant 36 is used in conjunction with a second implant 36. The two implants 36 are attracted to each other magnetically, at least one of which being a magnet. Hence, as used hereinafter when describing the remaining device embodiments, each implant will be referred to as a magnetic implant. This is to be interpreted as meaning the implant contains a magnet or an element that is attracted to a magnet and should not be interpreted as being limited to only magnets.

Figure 11B:
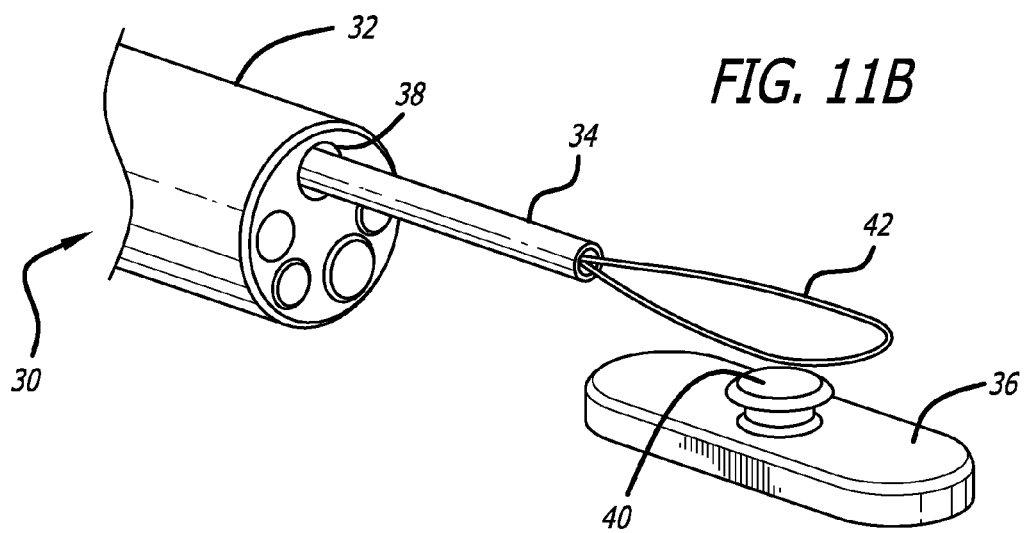

FIG. 11b illustrates unlocking the snare wire 42 and releasing the magnetic implant 36. The snare 42 is preferably formed of braided stainless steel cable or nitinol wire so that when the snare is unlocked to release the magnetic implant 36 it grows to a pre-formed size so that it may be easily released from the knob 40. Once the implants have been released, the snare may also be used to recapture the implant by re-snaring the knob on the implant. Although an external means for releasably attaching the implant to the delivery catheter using a knob feature has been shown, an implant housing is contemplated with internal releasable attachment features. The implants may be pulled apart by pulling on the delivery catheter. Once pulled apart, they may be repositioned or removed from the body.

Figure 12A:
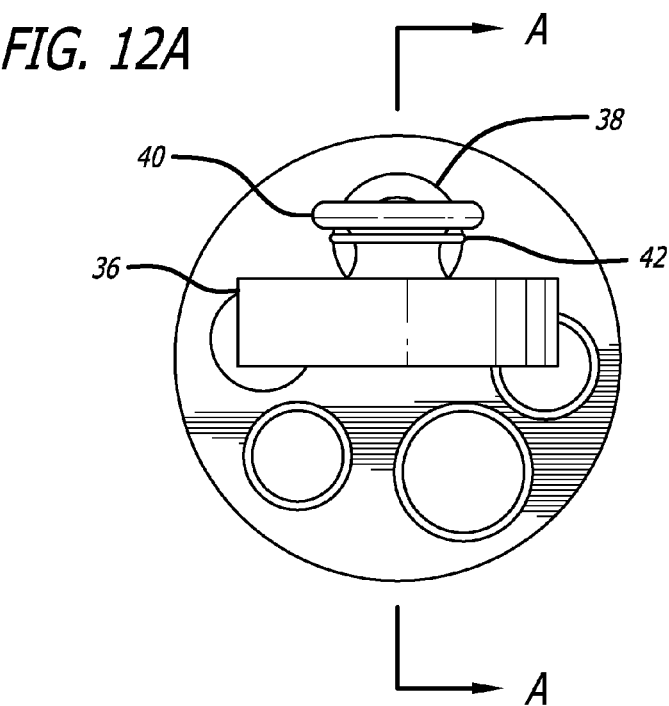
FIG. 12a is an end view of an embodiment of a device of the present invention attached to an embodiment of a delivery device of the present invention.
Figure 12B:
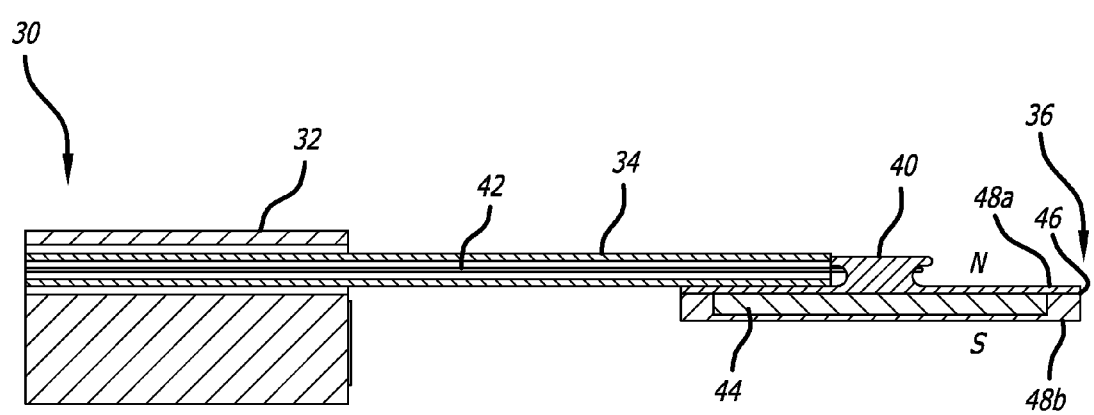

FIG. 12 shows a cross section of the distal portion of the endoscopic delivery device 30 in its locked condition. The magnetic implant 36 consists of a magnet 44 and housing 46. The housing consists of a top 48a and bottom 48b. The top 48a contains a knob feature 40 for holding onto the magnetic implant 36 with a snare 42. The magnetic implant incorporates rounded atraumatic features for ease of tracking the device through the body lumen prior to coupling and after the anastomosis has been created when the magnetic device/implant is exiting the body. The magnetic implant is preferably longer than it is wide and attached to the delivery catheter 34 so that the length is axially aligned with the endoscope 32. This small profile of the device relative to the profile of an endoscope aids in tracking the device ahead of the endoscope and allows variable length devices to be used depending on the size of anastomosis required. Additionally, the alignment of the magnetic implant aids in creating a side-to-side implant coupling and resulting anastomosis between vessels that are in close proximity or adjacent and aligned as shown in FIG. 15.

Figure 13:
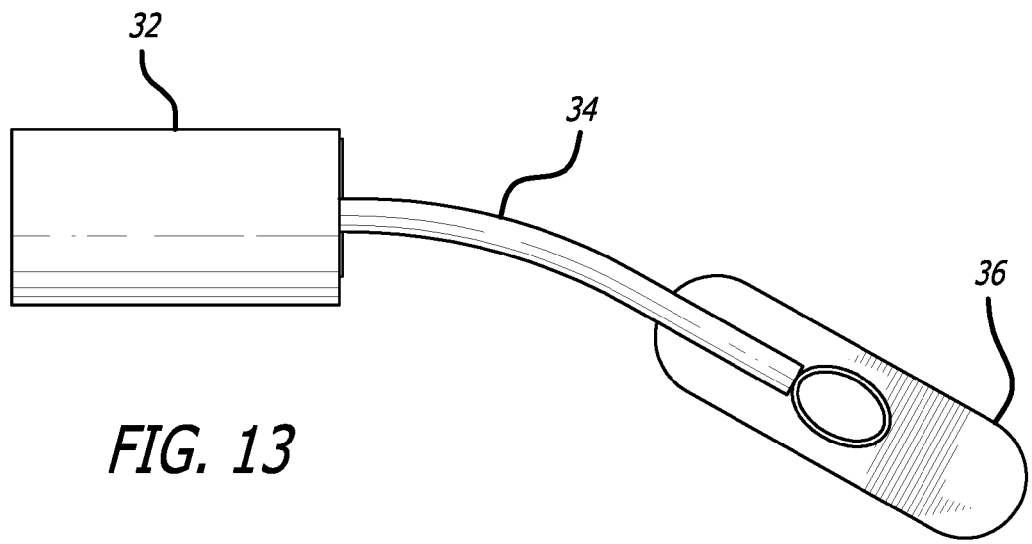
FIG. 13 is a plan view of an embodiment of a device of the present invention attached to an embodiment of a delivery device of the present invention.
Figure 14:
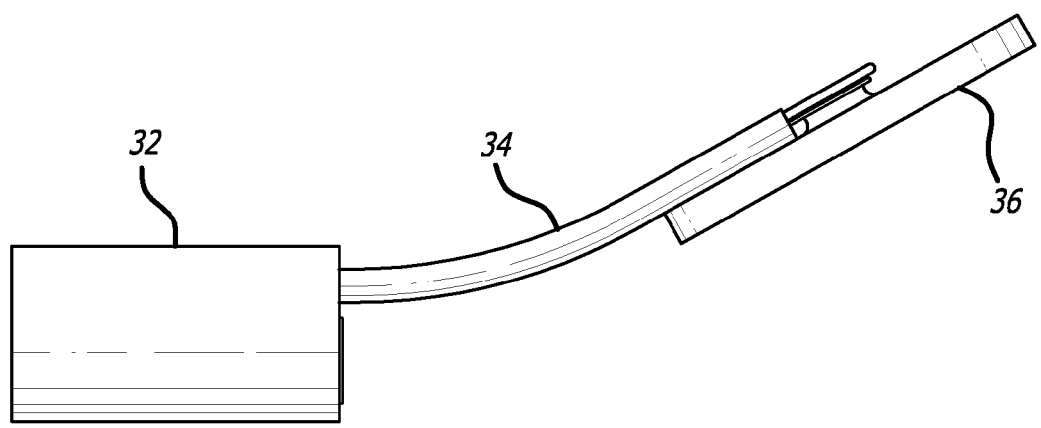
FIG. 14 is an elevation of an embodiment of a device of the present invention attached to an embodiment of a delivery device of the present invention.
Figure 15:
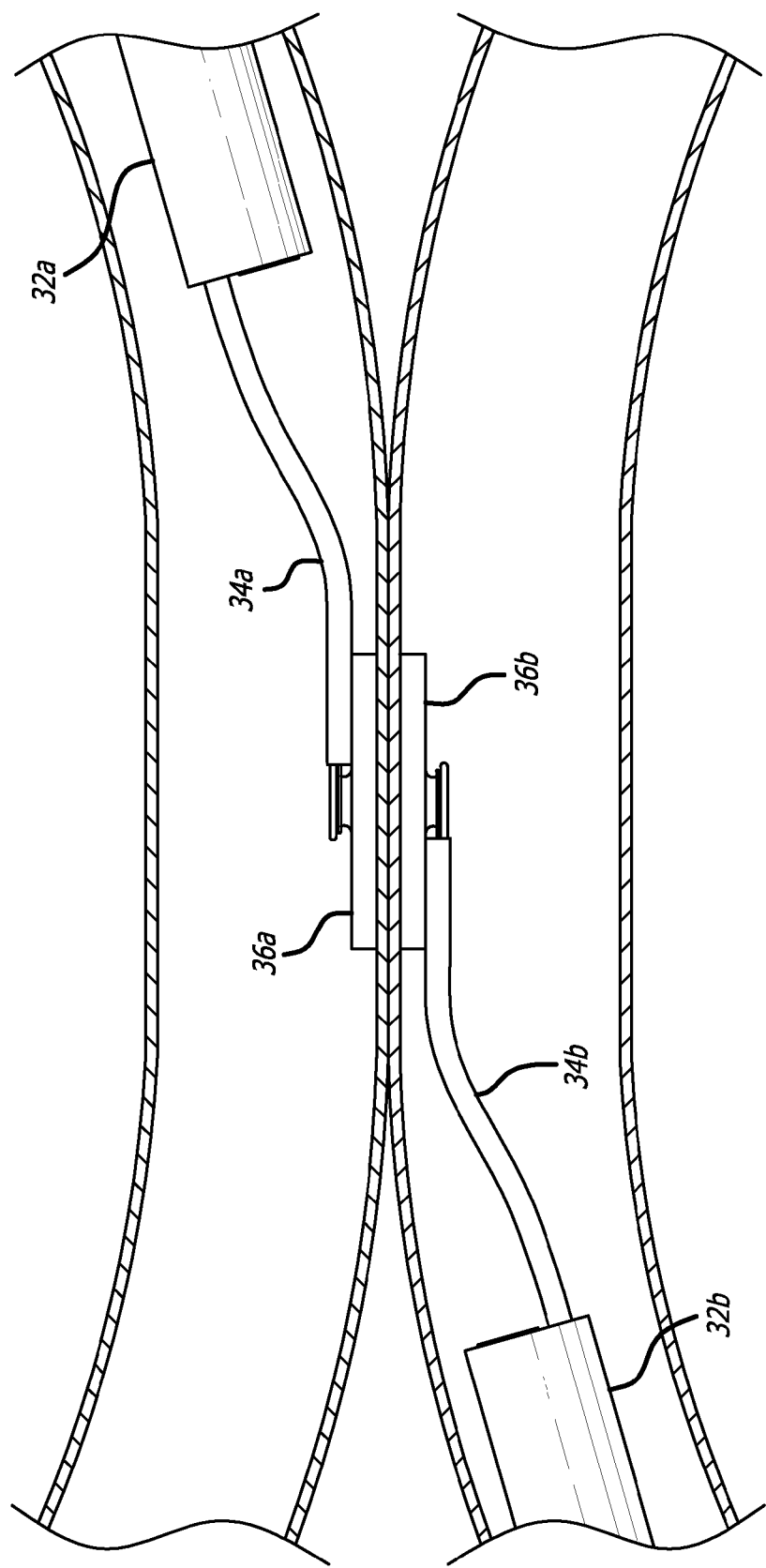
FIG. 15 is a side elevation of a pair of devices of an embodiment of the present invention being implanted in adjacent body lumens to form an anastomosis therebetween.

FIGS. 13-15 illustrate the movement and flexibility of the delivery catheter 34. The delivery catheter may move axially and be rotated relative to the endoscope 32. Having the ability to telescope out of the endoscope and rotate the magnetic implant 36 may allow the operator ease of accessing the target locations within the body as well as finely positioning the vessels and magnetic implants both axially and radially for coupling. As shown in FIG. 15, in this embodiment the delivery catheter 34a and attached magnetic implant 36a lead the endoscope 32a as it is tracked through the body vessel. Therefore, it may be advantageous if the distal tip of the delivery catheter is steerable to aid in tracking of the devices through the digestive tract. FIG. 13 shows a delivery catheter which articulates the magnetic implant in one direction while FIG. 14 shows a delivery catheter that articulates approximately orthogonal to the direction shown in FIG. 13. The catheter may be fabricated to have no articulation, or articulation in one direction, or articulation in the orthogonal direction, or both. The delivery catheter 34 preferably has excellent torsional stiffness so that it can rotate the magnetic implant 36 yet is flexible enough to allow the implants to easily attract and couple together.

For example, FIG. 15 shows two magnetic implants 36a and 36b coupled together in adjacent vessels. The figure shows that the axes of the endoscopes 32a and 32b are not aligned with the axis of the magnetic implants 36a and 36b. This is possible because the delivery catheters 34a and 34b are flexible and conform to the coupled magnetic implants 36a and 36b. The torsional stiffness and flexibility of the delivery catheter 34 may aid the operator with aligning and coupling the magnetic implants 36 so that the more rigid endoscopes do not have to be perfectly aligned in order for the magnetic implants 36a and 36b to couple. However, the flexibility of the endoscopes may be adequate to aid in coupling of the magnetic implants 36 and it may not be necessary to have a flexible catheter 34 to aid in coupling. The delivery catheters 34 preferably have good tensile strength so that they can easily pull the magnetic implants 36 apart should they need to be repositioned or removed. The delivery catheters 34 are preferably formed using standard component guide catheter techniques and may be constructed of a lamination of a polytetrafluoroethylene (Teflon) liner, a high density stainless steel braid, and a polymer outer jacket. The delivery catheter may be coated with a lubricious coating to aid in advancing down the lumen of the endoscope and in the body vessel. Also, the implant may be coated with a lubricious coating to aid in advancing through the body vessel. The coating may be a silicone or hydrophilic coating.

Figure 25:
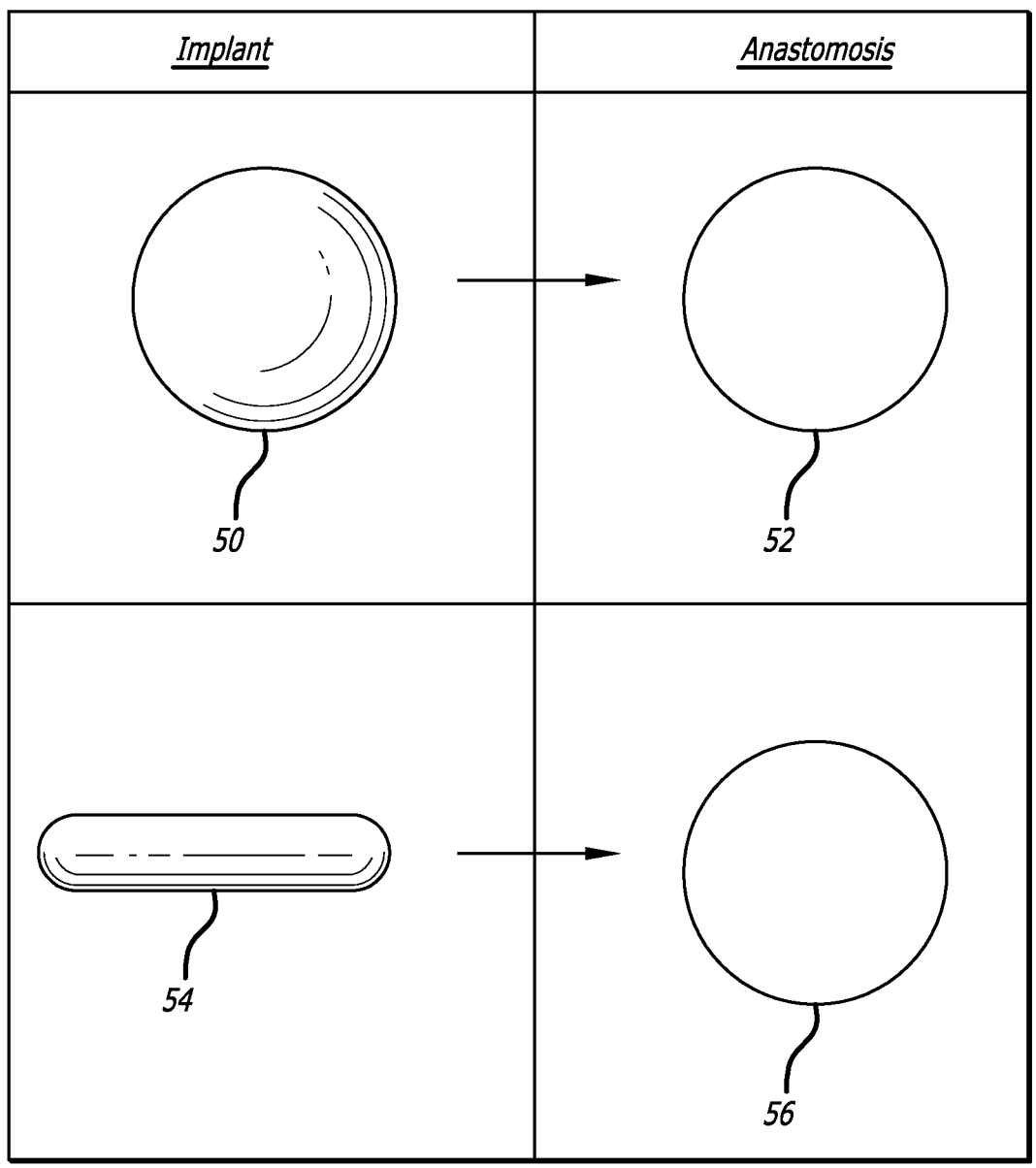
FIG. 25 is a comparison of device shapes and resulting anastomosis shapes.

Since the size of the anastomosis may affect the results of the partial bypass on weight loss or diabetes resolution, it is advantageous that a wide range of magnetic implant sizes are available to meet the needs of the range of sizes of human vessel anatomy. One aspect of the invention is that the resulting anastomosis size and shape is governed by the magnetic implant circumference and not necessarily its shape. As shown in FIG. 25 for example, if an anastomosis size of approximately 1.5" diameter was required, the operator could implant a round magnet 50 with a 1.5" diameter and a resulting approximately round anastomosis 52 of 1.5" diameter would result after healing was complete. However, tracking a round magnet 50 that was not collapsible through the digestive system would prove difficult as most endoscope diameters are approximately 0.5 inches by comparison. Alternatively, an approximately 1.85" long×0.375" wide magnet 54 of equal circumference to the round magnet 50 could easily be tracked through the digestive system if the long end of the magnet was aligned and advanced axially ahead of the endoscope. This implant would also create an approximately round anastomosis 56 of 1.5" diameter after healing was complete because even though the coupled magnetic implants will create a necrotic core of tissue the same size and shape as the magnets, the body over time remodels the shape of the implant to the native vessel shape which is approximately round. Hence, as the circumference of an elongate, relatively rectangular magnet having a width (w) and a length (l)=2(w)+2(l), and the circumference of a relatively round anastomosis has a circumference=2Πr. Therefore for a given desired implant width (w), the implant length (l) required to make an anastomosis having a desired radius (r) becomes Πr−w. With this in mind, typical endoscope working channels range in inner diameter from 1.5 mm to 7 mm. Thus, the magnetic implant widths (w) preferably fall within this range and, given the application discussed herein, and the most common endoscopes on the market, more preferably fall within the range of 1.5 mm to 3.7 mm.

Returning to FIG. 12, the magnet 44 is preferably a neodymium rare earth magnet. The magnetic poles are aligned through the thickness of the magnet so that the maximum magnetic force is achieved when the magnetic implants 36a and 36b are coupled as shown in FIG. 15. The bottom of the housing 48b can be smooth or have a surface roughness as the magnetic implants will align in either case because the inner lining of the vessels are very lubricious. Although lubricious, a rough surface on the bottom of the housing 48b may be advantageous once the magnets are coupled to prevent them from decoupling due to shear forces. The magnetic implant 36 may contain one magnet as shown in FIG. 12 or multiple smaller magnets. The housing 46 may be larger than the magnet 44 to distribute the magnetic force over a larger area. The housing 46 may be formed out of metal such as stainless steel, titanium, or other medical implant grade metals. Alternatively, the housing may be made of silicone or other medical implant grade polymers. Sections of the housing may be made out of biodegradable material. For instance, the knob 40 may be overmolded with biodegradable material onto the housing so that the knob would biodegrade after the magnetic implants are coupled. This would create a smaller profile of the coupled magnetic implants and may be easier to pass through the body once the anastomosis is created. The housing 46 may be formed of a top 48a and bottom 48b piece as shown or may be one integral body if formed using molding techniques. The housing's main functions are to provide a protective coating around the magnetic so that is does not corrode should it crack or fracture, provide attachment means to hold onto the magnet, distribute the force of a magnet over a surface area, and provide an atraumatic surface that passes easily through the digestive system. Although not preferred, a magnetically attracted ferrous metal core may take the place of the magnets in one of the magnetic implants. For instance, using FIG. 15 as a reference, the magnetic implant 36a may contain a neodymium magnet while the second implant 36b may contain a magnetically attracted ferrous metal core instead of a neodymium magnet. The ferrous metal core would preferably be the same size and shape as the neodymium magnet it replaces.

Figure 16A:
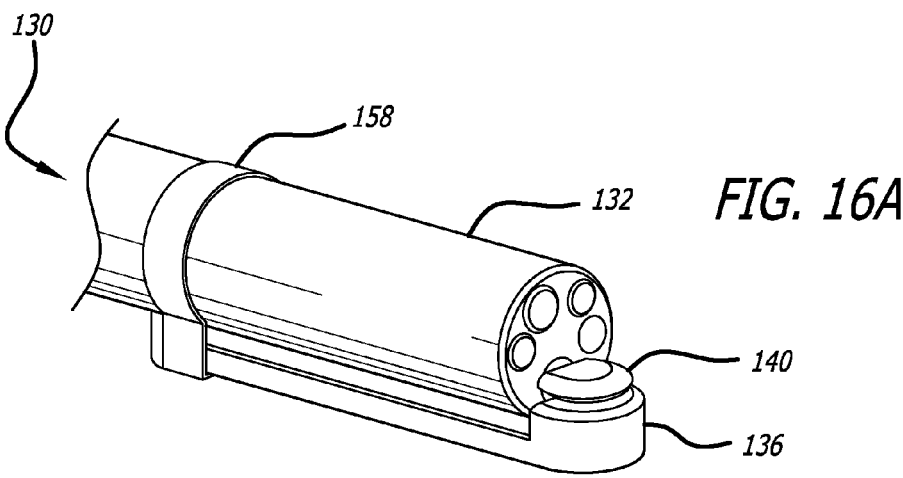
FIG. 16a is a perspective view of an embodiment of a device of the present invention attached to an embodiment of a delivery device of the present invention.
Figure 16B:
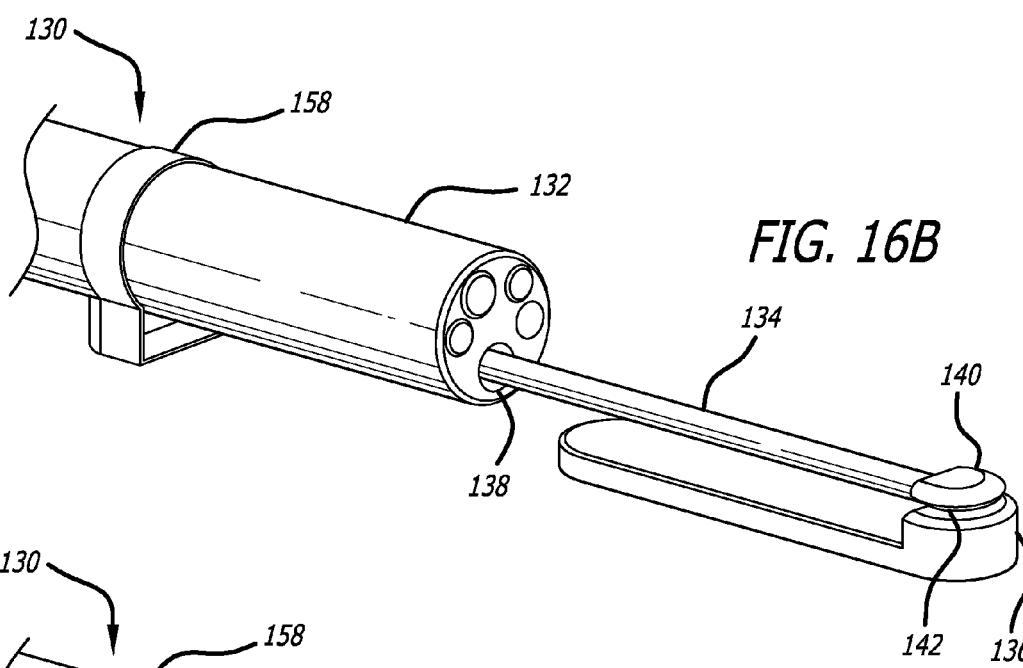
Figure 16C:
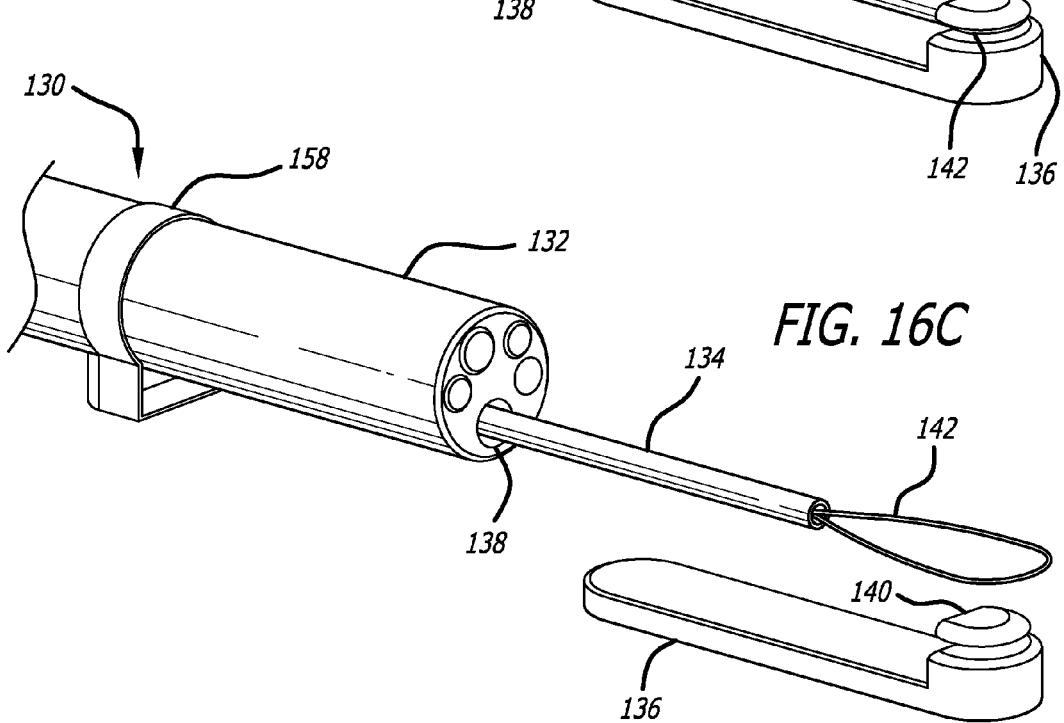

FIGS. 16a-16c show an alternative embodiment of an endoscopic delivery device 130 used according to the methods described previously to create a duodenum to transverse colon or ileum anastomosis. This embodiment is similar to the previous embodiment except that the magnetic implant geometry has changed to allow the implant to attach to the side of the endoscope while accessing the target anastomosis location. FIG. 16a shows a magnetic implant 136 docked to the end of an endoscope 132. The majority of the magnetic implant is long and thin except for the distal tip which contains a knob 140 similar to the previous embodiment. Most of the length of the magnetic implant resides on the side of the endoscope except for the leading edge containing the knob. As compared to the previous embodiment where the implant was completely in front of the scope, placing the implant in this position may allow the operator a better field of view as the implant cannot be blocking the view while gaining access to the target anastomosis location. However, the disadvantage is that the implant will increase the overall profile of the endoscope making it potentially more difficult to push through narrow regions such as the pylorus or ileocecal valve. A retention feature 158 may be attached to the outside of the endoscope 132 to prevent the proximal end of the implant 136 from bending away from the endoscope during retrograde movement of the endoscope. For instance, the proximal end of the implant may catch on the vessel wall or other anatomical features during retrograde movement. Similar to the previous embodiment, FIG. 16b illustrates that the implant 136 can be moved axially from the distal tip of the endoscope 132 Likewise, the endoscope is pre-assembled in similar fashion to the previous embodiment in that a delivery catheter 134 is loaded into the working channel 138 of the endoscope 132 and the magnetic implant 136 is releasably attached to the distal end of the delivery catheter 34 using a snare 142 that is wrapped around a knob feature 140 integral to the magnetic implant 36. FIG. 16c illustrates unlocking the snare wire 142 and releasing the magnetic implant 136.

Figure 17A:
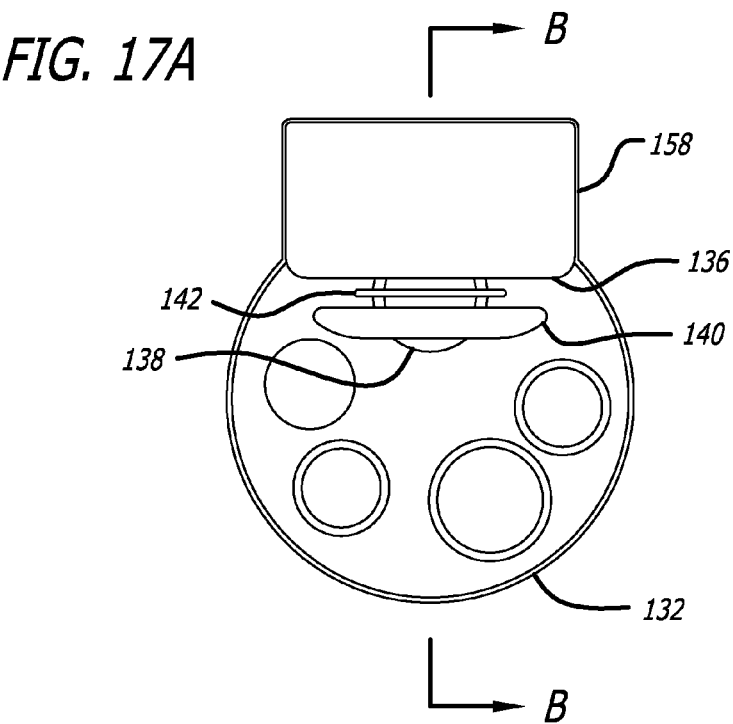
FIG. 17a is an end view of an embodiment of a device of the present invention attached to an embodiment of a delivery device of the present invention.
Figure 17B:
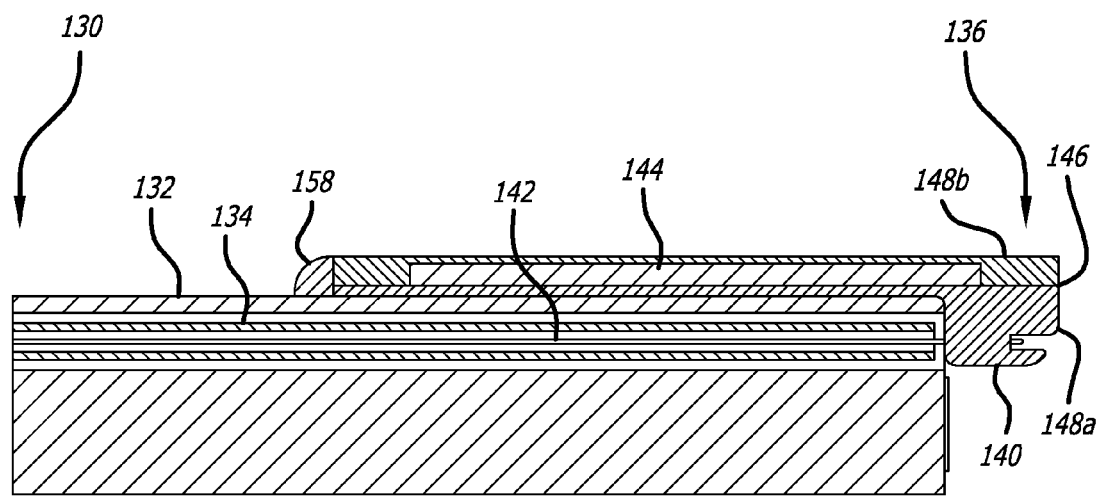

FIG. 17 shows a cross section of the distal portion of the endoscopic delivery device 130 in its locked condition. Similar to the previous embodiment, the magnetic implant 136 consists of a magnet 144 and housing 146. The housing consists of a top 148a and bottom 148b. The top 148a contains a knob feature 140 for holding onto the magnetic implant 136 with a snare 142. Although an external means for releasably attaching the implant to the delivery catheter using a knob feature has been shown, an implant housing is contemplated with internal releasable attachment features. As previously described, the magnetic implant incorporates rounded atraumatic features for ease of tracking the device through the body lumen prior to coupling and after the anastomosis has been created when the implant is exiting the body.

FIGS. 18a-18c show an alternative embodiment of an endoscopic delivery device 230 used according to the methods described previously to create a duodenum to transverse colon or ileum anastomosis. This embodiment is similar to the previous embodiments except that the magnetic implant geometry has changed to allow the implant to travel down the working channel of an endoscope instead of being pre-assembled at the distal end of the endoscope. One advantage of this embodiment as compared to the previous embodiments is that the endoscope may access the target anastomosis site in the duodenum and ileum or transverse colon without the potential challenges of the delivery catheter or magnetic implant extending out of the distal tip of the endoscope or to the side of the endoscope. This may allow the operator to use the endoscopes without the magnetic implant potentially obstructing the view, or adding to the effective diameter of the delivery device by the implant riding on the side of the scope, or adding to the overall stiffness of the endoscope by having a delivery catheter in the working channel and an implant leading the endoscope as the operator attempts to articulate the distal end of the scope and navigate through the vessels. Preferably, the endoscope is advanced through the vessel to the target implant location and the magnetic implant is subsequently advanced through the working channel to the distal tip of the endoscope. However advantageous it may seem to advance the delivery catheter and magnetic implant to the distal end of the endoscope after it has reached its target location as just described, the operator may pre-load the working channel with the delivery catheter and magnetic implant and advance it to the distal tip of the endoscope prior to or while tracking the endoscope through the body vessel to the target anastomosis location. Although the previously described embodiments may also work with advanced access tools, this embodiment is more readily available to be used with single of double balloon enteroscopes or other overtube or externally applied devices to a standard endoscope for gaining access deep into the small bowel from either a nasal, oral, or anal access location.

FIG. 18a illustrates that once the endoscope is navigated to the target anastomosis location, the magnetic implant 236 has been introduced into the endoscope 232 and advanced axially within the working channel 238 to the tip of the endoscope. FIG. 18b shows the implant 236 fully advanced out the endoscope 232 in a position for coupling. The implant is attached to the delivery catheter 234 by pulling a loop feature 260 attached to the implant into the lumen of the delivery catheter using a grabber 242 that resides within the lumen of the delivery catheter. FIG. 19. shows a detailed view of the connection of the magnetic implant 236 to the distal end of the delivery catheter 234. The loop 260 is back-loaded into the delivery catheter 234 by inserting the loop in the U-shaped jaw of the grabber 242 and pulling the grabber and loop into the delivery catheter. The height of the u-shaped feature is approximately the same size as the inner diameter of the delivery catheter so that the loop is trapped between the u-shaped jaw and the inner wall of the catheter. After the loop is pulled into the delivery catheter, the grabber is pulled tight relative to the delivery catheter and locked in a handle set (not shown) that would be positioned at the proximal end of the delivery catheter. While pulling tight, the implant 236 is rotated so the teeth 262 on the distal end of the delivery catheter 234 mate and insert into the notch 264 on the implant. The teeth transfer torque and rotation of the delivery catheter to the implant while the grabber 242 couples the implant axially to the catheter. These features allow the implant to be advanced axially and rotated relative to the endoscope to aid with fine positioning of the implant prior to and during coupling.

FIG. 18c shows the implant 236 released from the delivery catheter 234. The grabber 242 is advanced distally relative to the delivery catheter so that the loop 260 is able to leave the U-shaped jaw of the grabber. FIG. 20 shows a detailed view of the distal end of the delivery catheter and proximal end of the magnetic implant after release. Similar to the previous embodiments after release, the grabber 242 may re-capture the loop 260 if the implant 236 needs to be repositioned or removed from the body. Although an external means for releasably attaching the implant to the delivery catheter using a loop feature has been shown, an implant housing is contemplated with internal releasable attachment features.

Figure 22:
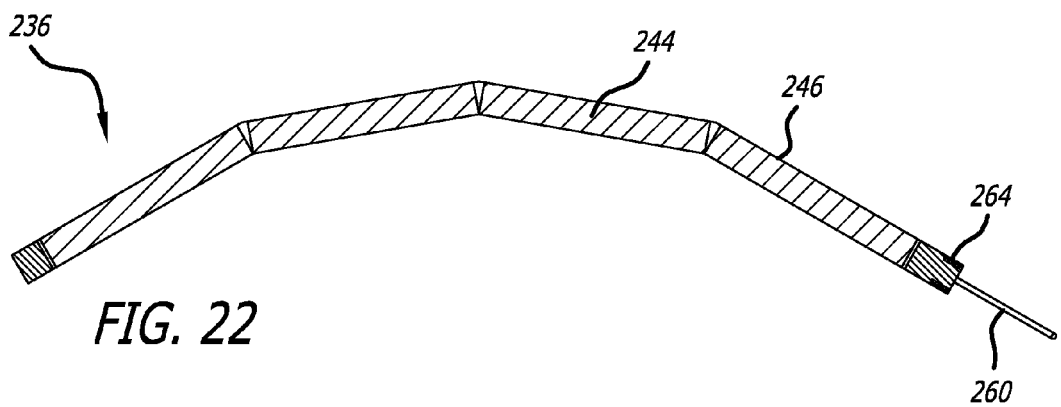
FIG. 22 is a cutaway view of an embodiment of a device of the present invention loaded into an embodiment of a delivery device of the present invention.

FIG. 21 shows the distal end of the endoscopic delivery device 230 in various cross sections. Section C-C shows the width of the magnets while Section D-D shows the thickness. FIG. 22 illustrates that the magnetic implant 236 is flexible so that it may be easily tracked through a flexible endoscope 232. The implant may consist of one magnet 244 or several depending on the overall length of the desired implant and the flexibility needed to access the target anastomosis location. The housing 246 may be constructed of an implant grade polymer of a durometer (hardness) that allows it to bend as shown. It may be fabricated and assembled by starting with an extrusion and assembling the magnets into the extrusion, or the magnets 244 may be insert molded. If insert molded, the polymer used should have melt temperature that does not degrade the magnetic properties of the magnet. The housing may also be fabricated out of an implant grade metal if the implant itself does not need to be flexible; however, it can be envisioned that a series of individual magnet are encapsulated in a metal housing could be attached in series with a cable, ribbon, or hitch feature coupling them all together where the ribbon or cable flexed so that the train of magnets could navigate a tortuous path. The ribbon or cable linking the series of magnets would preferably transfer rotational and axial movement from a releasably attached delivery catheter. As previously described, the implant incorporates rounded atraumatic features for ease of tracking the device into the body lumen prior to coupling and after the anastomosis has been created when the implant is exiting the body. The implant may be coated with a lubricious coating to aid in tracking down the lumen of the endoscope. Similar to the previous embodiments, the magnets are preferably neodymium rare earth magnets. The notched collar 264 and loop 260 may be insert molded into the housing or separately attached by reflowing them into the polymer of the housing or bonding them to the housing. The collar may be integrated into the housing instead of a separate component. The loop may be fabricated out of implant grade braided wire, solid wire, or nitinol wire. It may also be fabricated out of implant grade monofilament or braided polymer line.

Figure 23A:
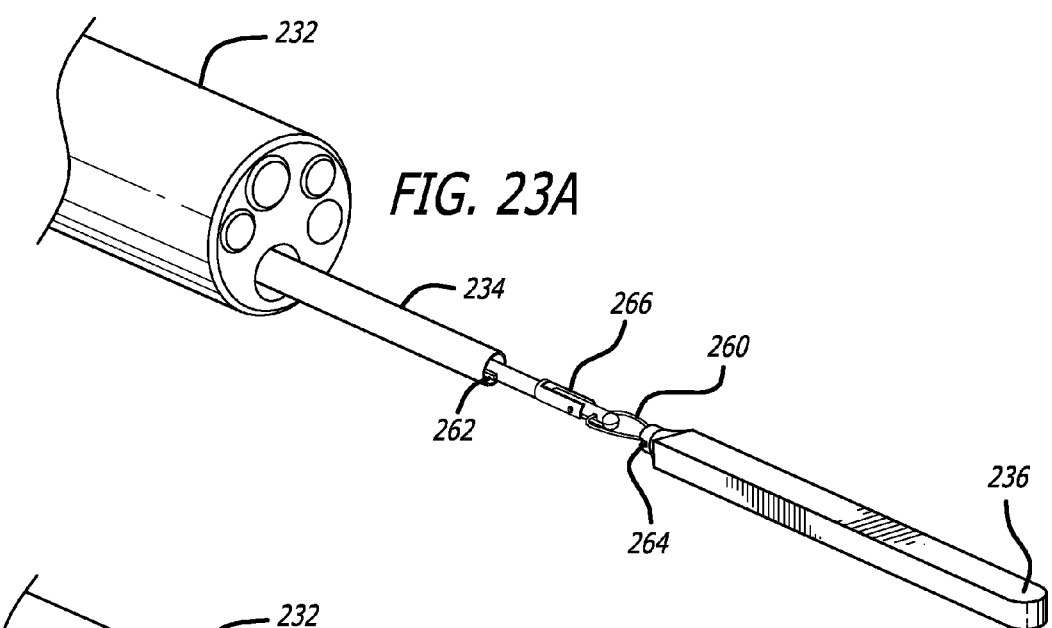
FIG. 23a is a perspective view of an embodiment of a device of the present invention attached to an embodiment of a delivery device of the present invention.
Figure 23B:
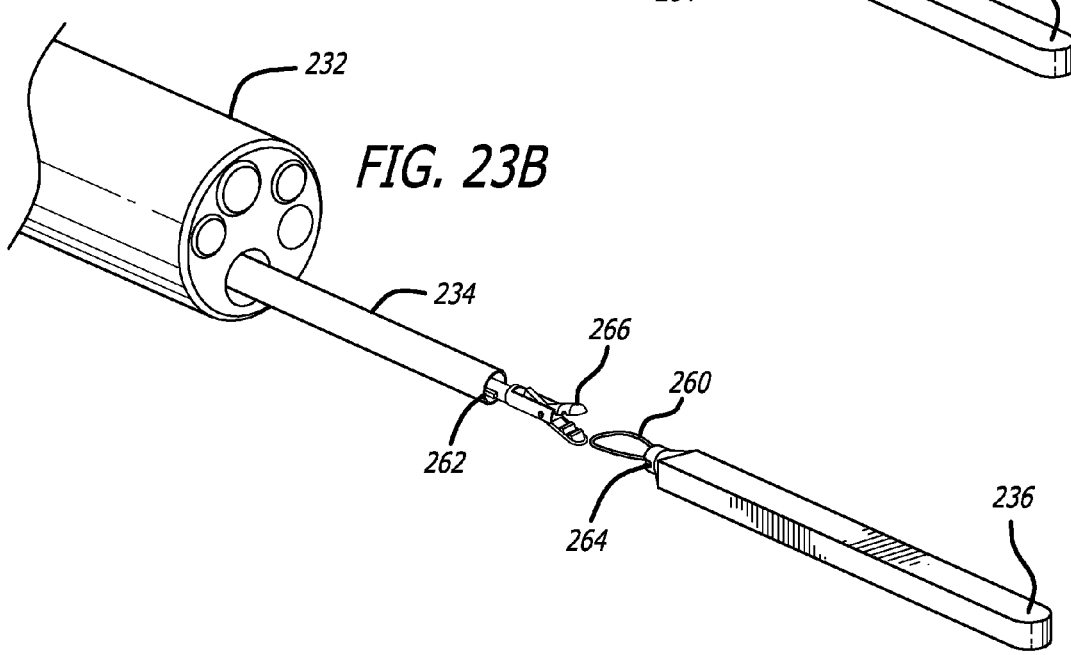

FIG. 23a shows an alternative attachment device for grabbing the loop 260 on the magnetic implant 236. In this figure, a mechanically actuated jaw grabber 266 is used to grab the loop instead of the grabber 242 shown in previous figures. The grabber has a slot cut through it to accept the loop. Similarly, the grabber 266 pulls the loop into the delivery catheter 234 and the teeth 262 slide into the slot 264 on the implant to transfer the torque as previously described. FIG. 23b shows the implant 236 released from the jaws of the grabber 242.

FIGS. 24a-24c show another variation of the previously described embodiment. This embodiment shows a different delivery catheter 334 with different releasable attachment features on the proximal end of the magnetic implant 336. This is to illustrate that there are many variations on how to releasably attach a thin magnetic implant that slides down the working channel of an endoscope to a delivery catheter. Those skilled in the art will appreciate that any deviations from what is shown would be encompassed in the spirit of the present invention. The difference in this variation is that the mechanically actuated jaw 366 is permanently attached to the distal tip of the delivery catheter 334 and does not slide within the lumen of the catheter. The torque transmitting teeth 262 and slot 264 from the previous embodiment have been replaced with a slot 372 feature in the mechanically actuated jaw and a mating bar 370 feature integrated into the housing 346 of the magnetic implant 336, respectively. The ball 368 feature integrated into the housing 346 transmits axially movement of the catheter 334 to the implant 336. FIG. 24d shows a detailed view of the distal tip of the catheter 334 and the proximal end of the magnetic implant 336. The slot 372 in the mechanically actuated jaw 366 is sized to mate and transmit torque to the bar 370 in the housing of the magnetic implant 336. The ball 368 and bar 370 may be bonded, molded, insert molded, or over molded onto the housing. Although an external means for releasably attaching the implant to the delivery catheter using a ball and bar feature have been shown, an implant housing is contemplated with internal releasable attachment features.

Since endoscopes have a wide range of working channel diameters. It may be advantageous to use a scope with a rather small working channel. This may translate into using a small magnetic implant that might not have enough strength to overcome the daily loads that the intestinal vessels experience from natural digestive processes and outside physical loads, therefore one magnetic implant may not give enough force or area to ideally create the desired anastomosis or maintain implant coupling due to internal or external loads. One aspect of the present invention is that multiple magnetic implants may be used to increase the strength and/or area of the anastomotic implant(s) in each vessel. FIG. 26 shows that the magnetic implants of the previously and subsequently described embodiments and variations may incorporate a second magnetic implant deployed to the side of the first implant to increase the anastomosis area and overall force clamping the vessels together at the anastomosis site. FIG. 27 shows a scenario where another magnetic implant 236 or 336 is stacked on top of a previously deployed magnetic implant 236 or 336 in the same vessel. This would double the force applied to create the anastomosis over the same area, therefore doubling the pressure on the trapped tissue. FIG. 28 shows a scenario where magnetic implants 236 or 336 have been stacked to the side and on top of previously applied magnetic implants. Magnetic implants may also be stacked in line (in front or behind) so that shorter implants could be placed in line to create a longer effective implant. The figures in no way illustrate all the combinations that those skilled in the art could easily contemplate.

Figure 29A:
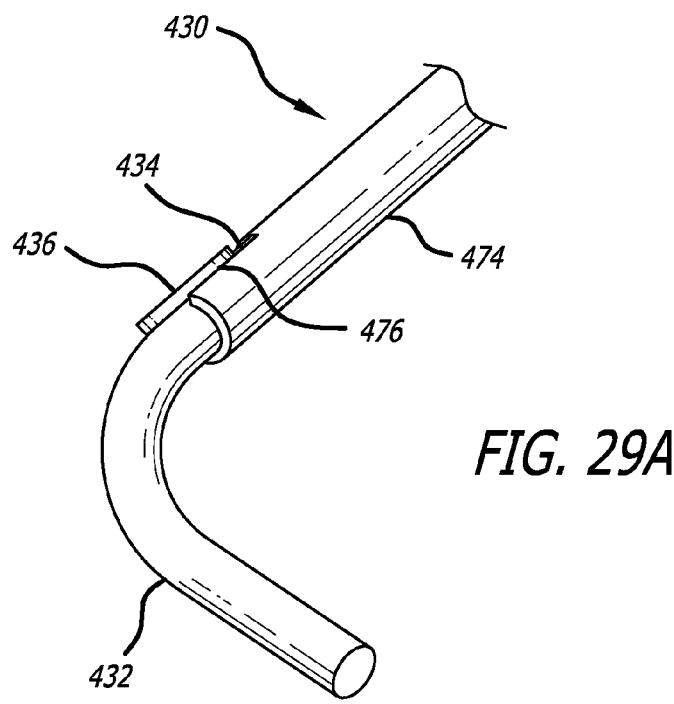
FIGS. 29a-d are a progression of perspective views of an embodiment of a delivery device of the present invention releasing an embodiment of a device of the present invention.
Figure 29B:
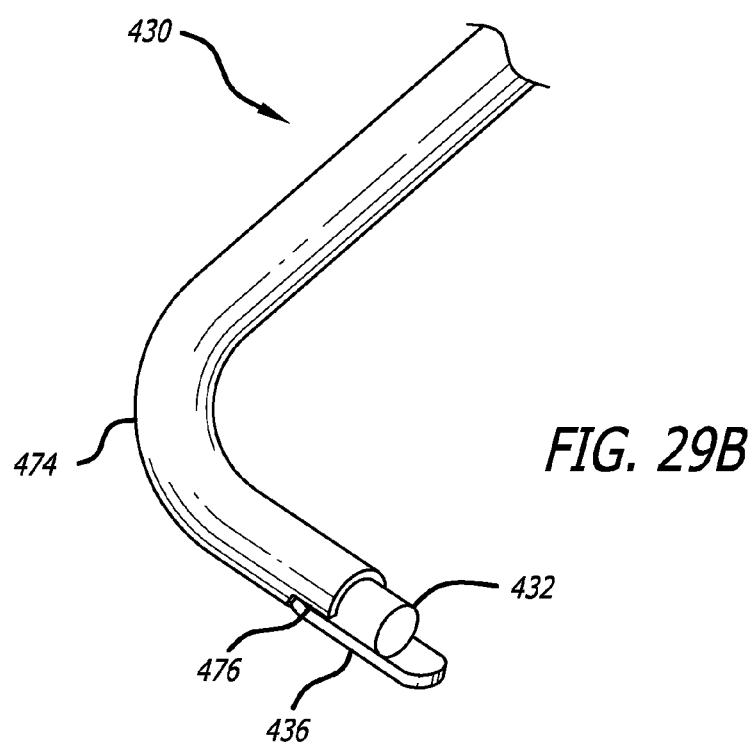
Figure 29C:
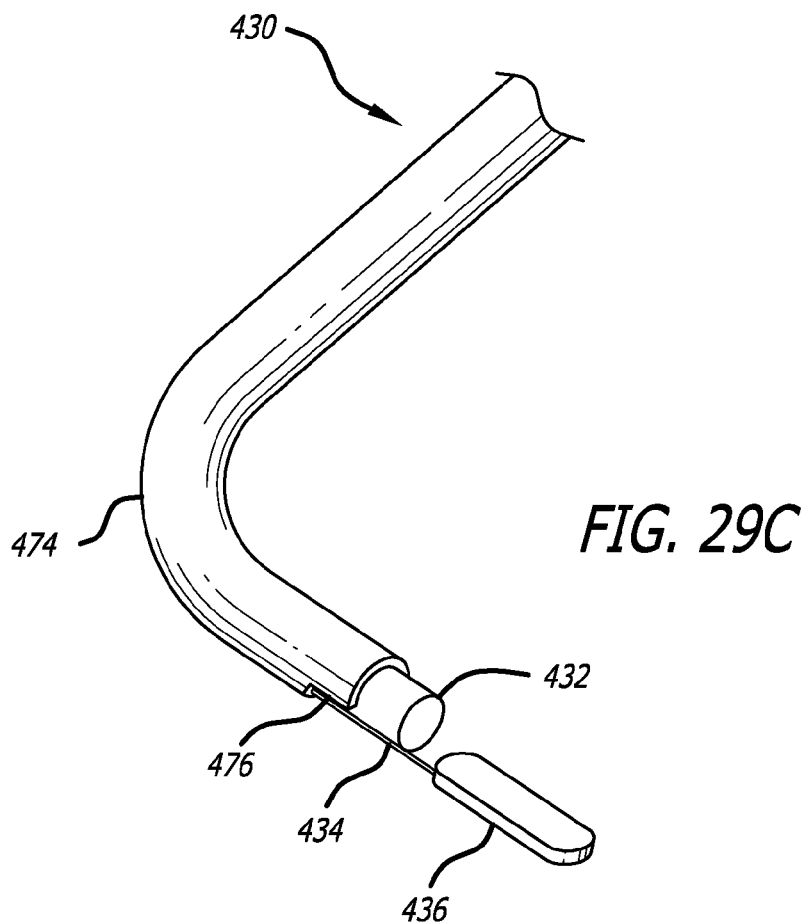
Figure 29D:
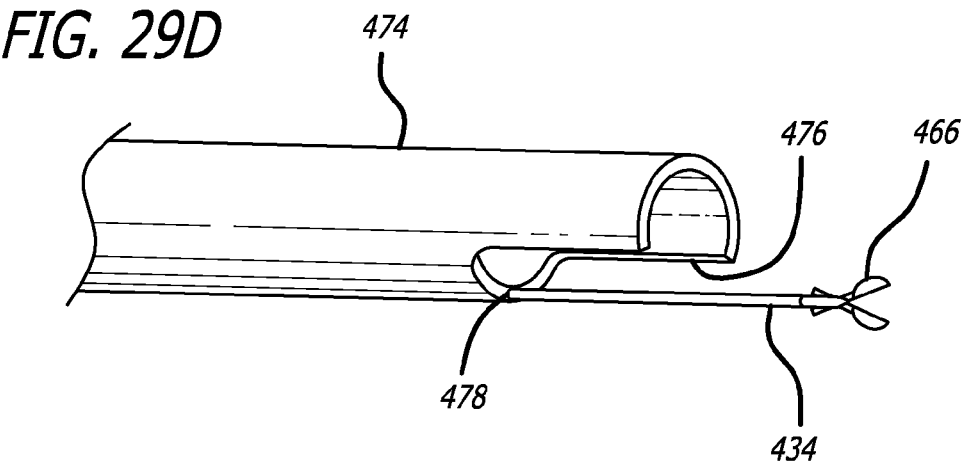

FIGS. 29a-29d show in stepwise fashion an embodiment of an endoscopic delivery device deploying a magnetic implant from an overtube assembled to the outside of an endoscope. The endoscopic delivery device 430 consists of a magnetic implant 436 releasably attached to a delivery catheter 434 that axially and rotationally moves within a lumen in the wall of an overtube 474. The overtube, delivery catheter, and magnetic implant assembly are back-loaded onto the endoscope 432 prior to inserting into the body. This view shows the overtube 474 in a retracted position away from the distal tip of the endoscope 432 allowing the articulating portion of the endoscope to be free from constrainment of the overtube. This feature allows the operator the ability to freely navigate through the body vessels without view obstruction of the magnetic implant 436 or hindrance of articulation of the endoscope. A grasping device 466 releasably holds the magnet in a slot 476 on the overtube 474. The notch on the overtube provides further constrainment of the magnet, especially in transferring torque and rotation to the implant about the endoscope. FIG. 29b illustrates that the overtube 474 can be moved axially in relation to the endoscope 432. Once the operator has navigated the distal tip of the endoscope to the desired target anastomosis location, the magnetic implant 436 is advanced to the tip of the endoscope 432 by moving the overtube 474 axially as shown. The ability to rotate the overtube about the endoscope allows the operator to position the implant in any radial direction to aid in achieving magnetic coupling with another magnetic implant in an adjacent vessel. FIG. 29c illustrates the delivery catheter 434 telescoping the magnetic implant 436 distal to the tip of the endoscope 432 to aid in magnetic coupling to another implant in an adjacent vessel. Also, the implant may be radially aligned by rotating the shaft of the delivery catheter. FIG. 29d shows the overtube 474, delivery catheter 434, and mechanically actuated jaw grabber 466 after the magnetic implant 436 has been released. The mechanically actuated jaw grabber 466 is attached to the delivery catheter 434. The delivery catheter 434 is located within a lumen 478 in the wall of the overtube 474. The mechanically actuated grabber may be designed to releasably attach to a feature that is internal or external to the magnetic implant. As described in the previous embodiments, the delivery catheter may be coated with a lubricious coating to aid in advancing down the lumen of the overtube. The inner diameter of the overtube may be coated to aid in advancing and rotating the overtube about the endoscope. Also, the implant may be coated with a lubricious coating to aid in advancing through the body vessel. The coating may be a silicone or hydrophilic coating.

Figure 30A:
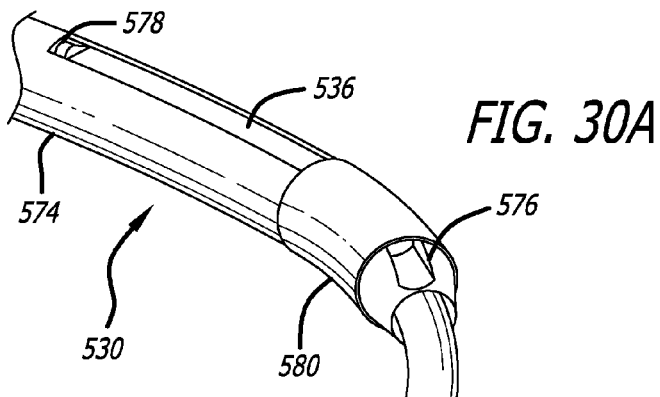
FIG. 30a is a perspective view of an embodiment of a device of the present invention attached to an embodiment of a delivery device of the present invention.
Figure 30B:
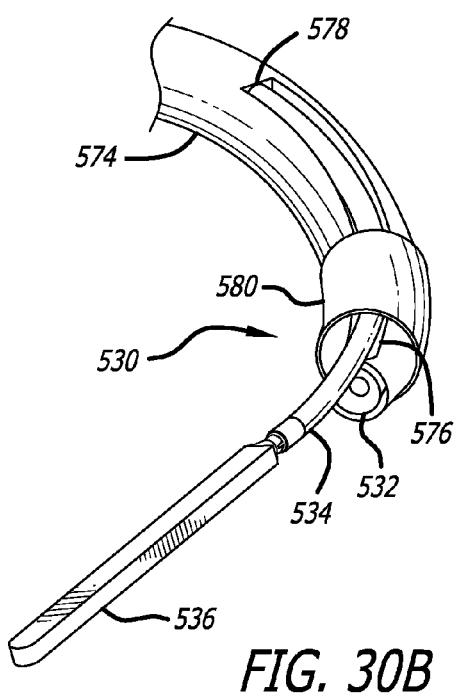
Figure 30C:
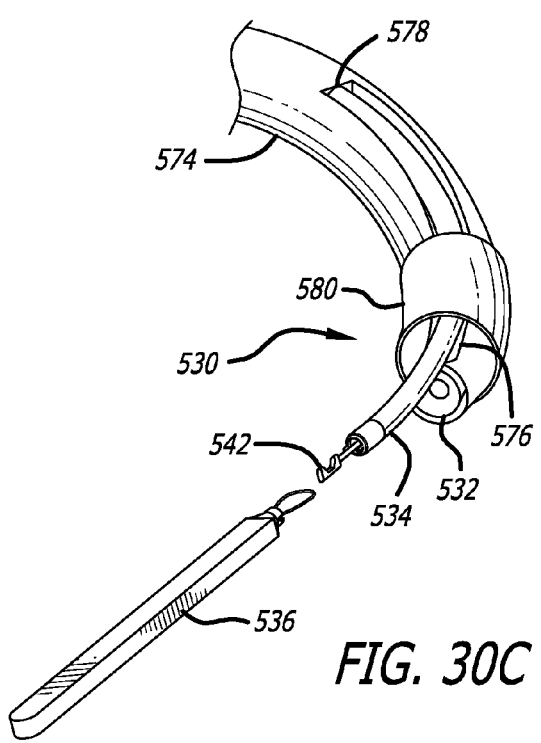

FIGS. 30a-30c show in stepwise fashion an alternative embodiment of an overtube endoscopic delivery device similar to the device previously described. This embodiment shows an overtube with a slot formed in the distal tip to receive a small profile magnetic implant as previously described in FIGS. 18-25. The overtube also has a lumen within its wall to accept a delivery catheter as previously described. The endoscopic delivery device 530 consists of a magnetic implant 536 releasably attached to a delivery catheter 534 that axially and rotationally moves within a lumen 578 in the wall of an overtube 574. Similar to the previous embodiment, the overtube, delivery catheter, and magnetic implant assembly are back-loaded onto the endoscope 532 prior to inserting into the body. FIG. 30a shows the overtube 574 in a retracted position away from the distal tip of the endoscope 532 allowing the articulating portion of the endoscope to be free from constrainment. The overtube 574 may be designed to integrate with any endoscope; however, the endoscope is preferably a gastroscope, colonoscope, or small diameter enteroscope. The distal end of the overtube is tapered to transition to the outer diameter of the endoscope. A balloon 580 may or may not be incorporated at the tip of the overtube 574 to allow single or double enteroscopy to aid in accessing target anastomosis locations deep with the bowel. As previously described in the embodiments, features within the delivery catheter and on the magnetic implant releasably attach the implant to the delivery catheter. The delivery catheter 534 holds the implant within the slot 576 of the overtube 574. As previously described, the slot on the overtube provides further constrainment of the magnetic implant, especially in transferring torque and rotation to the implant about the endoscope. Likewise, FIG. 30b illustrates the delivery catheter 534 telescoping the magnetic implant 536 distal to the tip of the endoscope 532 to aid in magnetic coupling to another implant in an adjacent vessel. Also, the implant may be radially aligned by rotating the shaft of the delivery catheter. FIG. 30c shows the delivery catheter 534 and grabber 542 after the magnetic implant 436 has been released. The delivery catheter, grabber and attachment features on the implant are for illustrative purposes as any combination of delivery catheter, grabber, and implant releasable attachment feature described in the previous embodiments may be incorporated as appropriate.

Figure 31A:
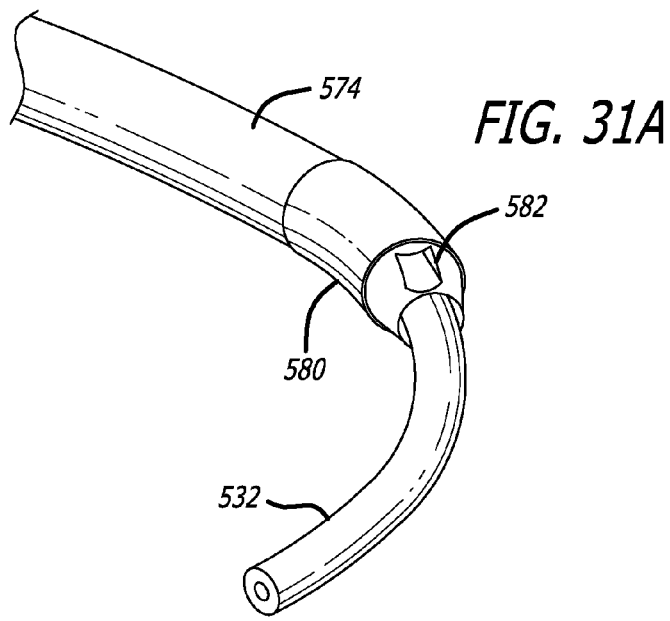
FIG. 31a is a perspective view of an embodiment of a device of the present invention attached to an embodiment of a delivery device of the present invention.
Figure 31B:
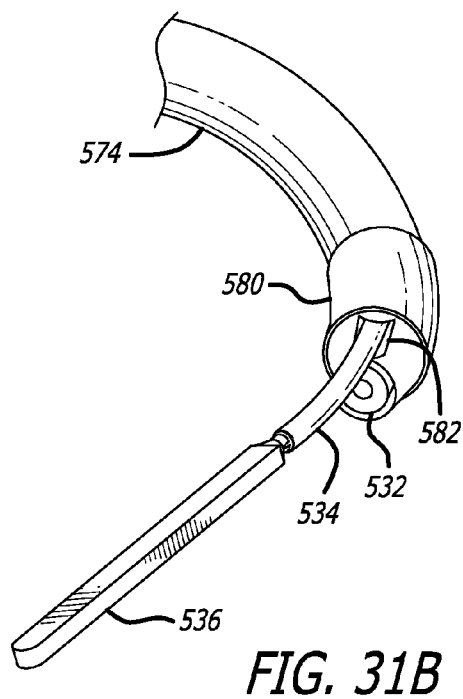
Figure 31C:
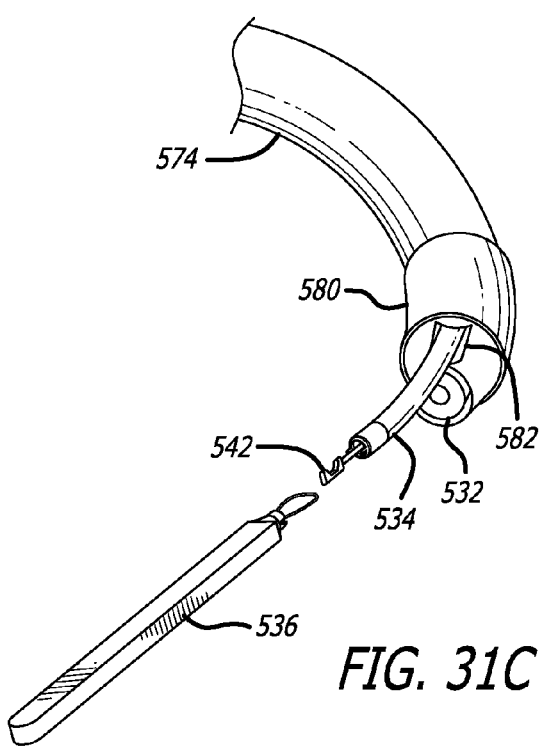

FIGS. 31a-31c show in stepwise fashion a variation of the previously described embodiment as shown in FIG. 30a-30c. The variation is different in that the slot or channel extends the entire length of the overtube instead of only at the distal tip of the overtube. Also, the channel is entirely within the wall of the lumen which allows the magnetic implant to be tracked along the entire length of the overtube. Similar to the previous embodiment, the overtube is back-loaded onto the endoscope 532 prior to inserting into the body, but the delivery catheter and magnetic implant may be loaded in the channel prior to inserting into the body. It may be easier to articulate the endoscope and navigate to the target anastomosis location without the increased stiffness of the magnetic implant and delivery catheter near the distal tip of the endoscope; therefore, it may be preferable to advance the implant and catheter after the target location is reached. However, it may not be necessary and may be preferable in some cases to telescope out of the distal tip to help introduce/guide the endoscope through the anatomy. Since the catheter and magnetic implant may be freely exchanged through the channel, the operator may deploy a second or multiple magnetic implants at the target location without removing the endoscopes from the target location. FIG. 31a shows the overtube 574 in a retracted position away from the distal tip of the endoscope 532. FIG. 31b illustrates the delivery catheter 534 telescoping the magnetic implant 536 distal to the tip of the endoscope 532 through the channel 582 in the overtube 574. FIG. 31c shows the variation after the magnetic implant has been released. As described in the previous embodiments, the delivery catheter may be coated with a lubricious coating to aid in advancing down the channel of the overtube. The inner diameter of the overtube may be coated to aid in advancing and rotating the overtube about the endoscope. Also, the implant may be coated with a lubricious coating to aid in advancing through the channel of the overtube. The coating may be a silicone or hydrophilic coating.

Although not preferred, another aspect of the invention for all the overtube embodiments is that the full profile of the overtube could be shorter and reside at the distal tip of the endoscope and not extend its full profile proximally out of the body. Instead, a smaller overtube profile just encompassing the delivery catheter could extend from the short, full profile section at the distal end of the endoscope proximally out of the body. Or, the overtube may only consist of a short, full profile at the distal tip of the endoscope with only the delivery catheter extending proximally out of the body.

Although the invention has been described in terms of particular embodiments and applications, one of ordinary skill in the art, in light of this teaching, can generate additional embodiments and modifications without departing from the spirit of or exceeding the scope of the claimed invention. For example, though the devices described herein are optimally designed for use in a probe, obviating the need for puncturing patient tissue or making incisions, one skilled in the art will appreciate that these devices could be used in surgical or laparoscopic procedures. Accordingly, it is to be understood that the drawings and descriptions herein are proffered by way of example to facilitate comprehension of the invention and should not be construed to limit the scope thereof.

We claim:

1. A system for forming an anastomosis in a digestive tract of a patient comprising:
    first and second probes, each probe defining at least one lumen slidingly housing an attachment mechanism and each probe having an optic lens;
    a first device carried by said first probe and attached thereto by said attachment mechanism, said first device comprising:
        a magnet;
        a housing at least partially encasing said magnet, said housing defining a connector releasably and repeatably engageable by said attachment mechanism;
    a second device carried by said second probe and attached thereto by said attachment mechanism, said second device comprising;
        an element attracted to said magnet of said first device;
        a housing at least partially encasing said element, said housing defining a connector releasably and repeatably engageable by said attachment mechanism;
    wherein:
        said first device has a length (l) and a width (w);
            wherein width (w) is narrow enough to fit within a working channel of a standard endoscope; and,
            wherein length (l) is related to a desired radius (r) of a resulting, substantially round anastomosis according to the formula $(l)=(\Pi)(r)-(w)$.

2. The device of claim 1 wherein (w) is between 1.5 mm and 7 mm.

3. The device of claim 2 wherein (w) is between 1.5 mm and 3.7 mm.

4. The device of claim 1 wherein said connector comprises a knob.

5. The device of claim 1 wherein said connector comprises a loop.

* * * * *